United States Patent [19]

Hall

[11] 4,436,596

[45] Mar. 13, 1984

[54] N-SUBSTITUTED-2-(R)-(SULFINIC ACID)-3-(S)-ACYLAMIDO)-4-OXO-AZETIDINES AND PROCESS

[75] Inventor: David A. Hall, Indianapolis, Ind.

[73] Assignee: Eli Lilly and Company, Indianapolis, Ind.

[21] Appl. No.: 442,075

[22] Filed: Nov. 16, 1982

[51] Int. Cl.$^3$ ............... C25C 3/00; C07D 205/08; C07D 403/12; C07D 405/12

[52] U.S. Cl. .................. 204/59 R; 204/72; 204/73 R; 260/239 A; 260/245.4; 260/330.3; 260/330.9; 544/28; 544/30

[58] Field of Search ............ 204/59 R, 72, 73 R, 204/75

[56] References Cited

U.S. PATENT DOCUMENTS 4,042,472 8/1977 Hall ............... 204/73 R
4,159,266 6/1979 Kukolja ............ 260/239 A
4,293,493 10/1981 Kukolja et al. ........ 260/239 A

OTHER PUBLICATIONS

B. Lamm and J. Simonet, *Acta Chem. Scand.*, B 28, (1974), pp. 147–152.
J. Y. Pape and J. Simonet, *Electrochimica Acta*, 23, pp. 445–449 (1978).
C. M. Pant and R. J. Stoodley, *J. C. S. Perkin I,* 1978, pp. 1366–1369.

*Primary Examiner*—F. Edmundson
*Attorney, Agent, or Firm*—Paul C. Steinhardt; Arthur R. Whale

[57] ABSTRACT

N-substituted-2-(R)-(sulfinic acid)-3-(S)-(acylamino)-4-oxo-azetidines, which are useful as intermediates in 1-oxa β-lactam antibiotics, are synthesized by electrolytic reduction of 7-(S)-acylamino-3-hydroxymethyl-3-cephem-4-carboxylic acid compounds.

31 Claims, No Drawings

N-SUBSTITUTED-2-(R)-(SULFINIC ACID)-3-(S)-(ACYLAMIDO)-4-OXO-AZETIDINES AND PROCESS

SUMMARY OF THE INVENTION

This invention is directed to intermediates and a process for making them that are part of a new synthesis to 1-oxa β-lactam antibiotics. The intermediates are N-substituted-2-(R)-(sulfinic acid)-3-(S)-(acylamido)-4-oxo-azetidines. The intermediates also encompass of course, sulfinic acid salts. The N-substituents are 3-hydroxymethyl-buten-2-yloic acid and the corresponding carboxylic acids and salts, where the double bond can be in the 2 or 3 position.

The process for making these intermediates encompasses the electrolytic reduction of a 7-(S)-acylamino-3-hydroxymethyl-3-cephem-4-carboxylic acid and the corresponding carboxylic acid salts and esters.

DETAILED DESCRIPTION

One aspect of this invention relates to azetidinone sulfinic acid compounds of the formula 1

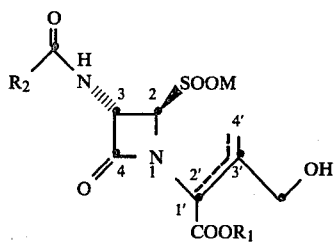

wherein:

M is hydrogen or is a lithium, potassium, sodium, ammonium or a substituted ammonium cation;

R$_1$ is hydrogen, a carboxylic acid protecting group, lithium, potassium, sodium, ammonium or substituted ammonium cation;

R$_2$ is
  a. C$_1$ to C$_7$ alkyl, C$_3$ to C$_7$ alkenyl, chloromethyl, dichloromethyl, 4-carboxybutyl, 4-formylbutyl, 4-protected carboxybutyl, 4-protected amino-4-protected carboxybutyl; or
  b. C$_1$ to C$_6$ alkoxy, C$_3$ to C$_6$ cycloalkyloxy, benzyloxy or substituted benzyloxy, wherein the substituents are one to three groups chosen from the group consisting of C$_1$ to C$_4$ alkyl, C$_1$ to C$_4$ alkoxy or chloro; or
  c. 1,4-cyclohexadienyl, phenyl or substituted phenyl, wherein the substituents are one or two groups chosen from the group consisting of chlorine, bromine, hydroxy, trifluoromethyl, C$_1$ to C$_4$ alkyl, C$_1$ to C$_4$ alkoxy, carboxy, carboxymethyl, hydroxymethyl, aminomethyl and protected aminomethyl; or
  d. an arylalkyl group of the formula R'—(O)$_m$—CH$_2$— wherein R' is 1,4-cyclohexadienyl, phenyl or substituted phenyl as defined above, and m is 0 or 1; or
  e. a substituted arylalkyl group of the formula

wherein R" is R' as defined above, 2-thienyl, or 3-thienyl; W is hydroxy, carboxy, protected carboxy, amino or protected amino; or
  f. a heteroarylmethyl group of the formula

R'''—CH$_2$— wherein R''' is 2-thienyl, 3-thienyl, 2-furyl, 3-furyl, 2-thiazolyl, 5-tetrazolyl or 1-tetrazolyl; with the limitation that when the compound is of formula 2

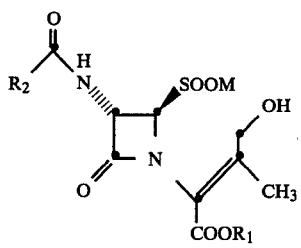

R$_2$ is 1,4-cyclohexadienyl, phenyl or substituted phenyl, wherein the substituents are one or two groups chosen from the group consisting of chlorine, bromine, hydroxy, trifluoromethyl, C$_1$ to C$_4$ alkyl, C$_1$ to C$_4$ alkoxy, carboxy, carboxymethyl, hydroxymethyl, aminomethyl and protected aminomethyl.

In a further aspect of this invention there is provided a process for preparing the above azetidinone sulfinic acids which comprises electrolytically reducing at a potential at or above the reduction potential required for the cleavage of the sulfone to C$_2$ bond of a cephalosporin sulfone compound of the formula

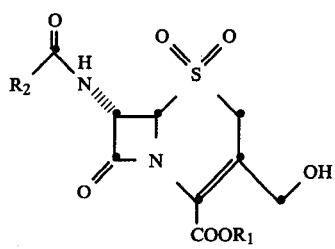

in a solvent chosen from the group consisting of a polar organic solvent, water, and a mixture of the two, all of which are stable under the conditions of the electrolysis, and
  (a) when the solvent used is a polar organic solvent or a mixture of water and a polar organic solvent, a proton source comprised of a carboxylic acid having a pKa between about 0 to about 5 in an amount equal to at least one molar equivalent per molar equivalent of cephalosporin sulfone; or
  (b) when the solvent used is water, maintaining the pH of the aqueous medium between about 3 to about 9;
at a temperature above about the freezing point of the liquid medium used to about 40° C.; wherein the electrolytic reduction is carried out in the presence of a catholyte selected from the group consisting of an alkali metal salt, ammonium and substituted ammonium salts.

In the above formula for the cephalosporin sulfone compound, $R_1$ and $R_2$ have the same meaning as they do for the azetidinone sulfinic acid compounds of formula 1, For convenience in describing the present invention, the following discussion will be in two parts, one part concerning the azetidinone sulfinic acid compounds with a double bond in the 3',4'-position, and the process for the production thereof, and the second part encompassing a similar discussion of the azetidinone sulfinic compounds with the double bond in the 2',3'-position.

A. The 3',4'-unsaturated ("$\beta,\gamma,$") azetidinone sulfinic acids.

The 3',4'-unsaturated azetidinone sulfinic compounds of this invention having the formula 3

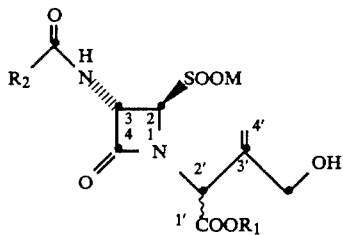

3 are referred to as the "$\beta,\gamma$ sulfinic acids". This invention encompasses both the 2'-(S) isomer having the partial formula

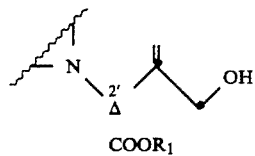

and the 2'-(R)isomer, having the partial formula

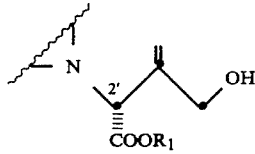

The $\beta,\gamma$ sulfinic acids of this invention also have the 2-(R) and the 3-(S) configuration. These configurations at the 2 and 3 carbons are the correct stereochemistry for the formation of the epi-oxazoline compounds, compounds that are intermediates in the synthesis of 1-oxa $\beta$-lactam antibiotics.

As used in the above general description of the azetidinone sulfinic compounds, the term "$C_1$ to $C_7$ alkyl" refers to methyl, ethyl, n-propyl, n-butyl, isobutyl, pentyl, n-hexyl, n-heptyl, cyclohexyl, and like aliphatic hydrocarbon chains. "$C_3$ to $C_7$ alkenyl" refers to the unsaturated hydrocarbon chains such as propenyl (allyl), butenyl, pentenyl, hexenyl, heptenyl, and the like. The term "$C_1$ to $C_6$ alkoxy" refers to groups such as methoxy, ethoxy, n-propoxy, isopropoxy, n-butoxy, iso-butoxy, valeroxy, hexyloxy, and the like.

The term "$C_3$ to $C_6$ cycloalkyloxy" refers to groups such as cyclopropyloxy, cyclobutyloxy, cyclopentyloxy and cyclohexyloxy.

The term "substituted benzyloxy" refers to compounds such as 3-chlorobenzyloxy, 2-methyl-3-chlorobenzyloxy, 2,4-dimethylbenzyloxy, 4-n-propylbenzyloxy, 4-n-butylbenzyloxy, 2-ethyl-4-n-propylbenzyloxy, 2-methoxybenzyloxy, 2,4-dimethoxybenzyloxy, 4-ethyloxybenzyloxy, 3-chloro-4-ethyloxybenzyloxy, 2-methyl-3-chlorobenzyloxy, 4-ethyloxybenzyloxy, 4-t-butylbenzyloxy, 2,4-dichlorobenzyloxy, 2,3,4,-trimethoxybenzyloxy, 2,3,4-trimethylbenzyloxy, 3-propyloxybenzyloxy, and the like.

The term "substituted phenyl" refers to a mono- or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3-chloro-4-bromophenyl,2-fluorophenyl and the like; a mono- or dihydroxyphenyl group such as 4-hydroxyphenyl, 3-hydroxyphenyl, 2,4-dihydroxyphenyl and the like; a mono- or disubstituted lower alkylphenyl group such as 4-methylphenyl, 2,4-dimethylphenyl, 2-methylphenyl, 4-isopropylphenyl, 4-ethylphenyl, 3-n-propylphenyl and the like; a mono- or disubstituted lower alkoxyphenyl group for example, 2,6-dimethoxyphenyl, 4-methoxyphenyl, 3-ethoxyphenyl, 4-isopropoxyphenyl, 4-t-butoxyphenyl, 3-ethoxy-4-methoxyphenyl; a mono- or disubstituted trifluoromethylphenyl group such as 4-trifluoromethylphenyl, 3,4-di(trifluoromethyl)phenyl, and the like; a mono- or disubstituted carboxyphenyl group, such as 4-carboxyphenyl, 2-carboxyphenyl, 3-carboxyphenyl, 2,4-dicarboxyphenyl, and the like; a phenyl ring substituted by 1 or 2 carboxymethyl groups, such as 2-carboxymethylphenyl, 3-carboxymethylphenyl, 4-carboxymethylphenyl, 2,3-dicarboxymethylphenyl, and the like; a phenyl moiety that is mono- or disubstituted by hydroxymethyl, resulting in benzyl alcohol type moieties, e.g. 2-(hydroxymethyl)phenyl, 4-(hydroxymethyl)phenyl, 3-hydroxymethyl)phenyl, 3,4-di(hydroxymethyl)phenyl, and the like; phenyl groups mono- or disubstituted by aminomethyl groups, resulting in benzylamine type moieties, e.g. 2-(aminomethyl)phenyl, 4-(aminomethyl)phenyl, 2,3-di(aminomethyl)phenyl, and the like. It should be noted that phenyl groups disubstituted with bromine are excluded from the above definition. The term "substituted phenyl" also represents disubstituted phenyl groups wherein substituents can be different, for example, 3-methyl-4-hydroxyphenyl, 3-chloro-4-hydroxyphenyl, 2-methoxy-4-bromophenyl, 4-ethyl-2-hydroxyphenyl, 2-hydroxy-4-chlorophenyl, 3-trifluoromethyl-4-hydroxyphenyl, 2-carboxy-4-ethoxyphenyl, 2-(aminomethyl)-4-(hydroxymethyl)phenyl, 4-carboxymethyl-2-methylphenyl, 3-(hydroxymethyl)-4-chlorophenyl, and like disubstituted phenyl groups bearing different substituents.

Illustrative of the acyl groups

when $R_2$ is a group of the formula $R'—(O)_m—CH_2—$, m is O and R' is 1,4-cyclohexadienyl, phenyl or substituted phenyl as defined above, are 2-(cyclohexa-1,4-dien-1-yl)acetyl, phenylacetyl, 4-chlorophenylacetyl, 3- hydroxyphenylacetyl, 4-hydroxy-3-methylphenylacetyl, 4-hydroxyphenylacetyl, 4-bromophenylacetyl, 4-ethoxyphenylacetyl, 3,4-dimethoxyphenylacetyl, and the like; and when m is 1, representative acyl groups are phenoxyacetyl, 3-hydroxyphenoxyacetyl, 4-hydroxyphenoxyacetyl, 4-chlorophenoxyacetyl, 3,4-dichlorophenoxyacetyl, 2-chlorophenoxyacetyl, 4-methoxyphenoxyacetyl, 2-ethoxyphenoxyacetyl, 3,4dimethylphenoxyacetyl, 4-isopropylphenoxyacetyl, 4-methyl-2-carboxyphenoxyacetyl, 4-aminomethylphenoxyacetyl, 4-carboxyphenoxyacetyl, 4-carboxymethylphenoxyacetyl, 3-trifluoromethylphenoxyacetyl, 2-hydroxymethylphenoxyacetyl, 2-aminophenoxyacetyl, and like acyl groups.

Illustrative of the acyl groups

wherein R₂ is a substituted arylalkyl group of the formuls

wherein R" is the same as R' defined above or 2-thienyl or 3-thienyl, are the hydroxy substituted arylalkyl groups such as the 2-hydroxy-2-phenylacetyl group of the formula

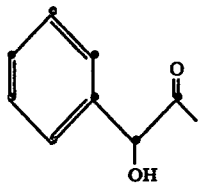

and similar groups wherein the phenyl ring is substituted, for example, 2-hydroxy-2-(4-methoxyphenyl)acetyl, 2-hydroxy-2-(3-chloro-4-hydroxyphenyl)acetyl, 2-hydroxy-2-(4-hydroxyphenyl)acetyl, 2-hydroxy-2-(3-bromophenyl)acetyl, 2-hydroxy-2-(3,5-dichloro-4-hydroxyphenyl)acetyl, 2-hydroxy-2-(3-chloro-4-methoxyphenyl)acetyl, 2-hydroxy-2-(3-chlorophenyl)acetyl, and like groups; the 2-carboxy-2-phenylacetyl group or 2-(protected carboxy)phenylacetyl group of the formula

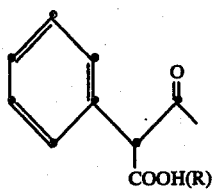

and similar groups wherein the phenyl ring is substituted, for example, 2-protected carboxy-2-phenylacetyl, 2-tert-butoxycarbonyl-2-phenylacetyl, 2-benzyloxycarbonyl-2-(4-chlorophenyl)acetyl, 2-carboxy-2-(4-methoxyphenyl)acetyl, 2-carboxy-2-(4-hydroxyphenyl)acetyl, and like groups; the 2-amino-2-phenylacetyl or 2-(protected amino)-2-phenylacetyl of the formula

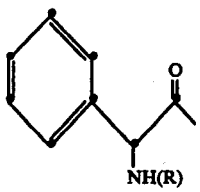

wherein R is an amino protecting group, and similar groups wherein the phenyl ring is substituted, for example, 2-amino-2-phenylacetyl, 2-amino-2-(4-chlorophenyl)acetyl, 2-amino-2-(4-hydroxyphenyl)acetyl, and like acyl groups; and also groups such as 2-amino-2-(2-thienyl)acetyl, 2-amino-2-(2-furyl)acetyl, 2-amino-2-(1,4-cyclohexadien-1-yl)acetyl and the like.

Representative of the acyl group

when R₂ is a heteroarylmethyl group of the formula

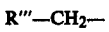

wherein R'" is 2-thienyl, 3-thienylacetyl, 2-furylacetyl, 3-furylacetyl, a 2-thiazolylacetyl group of the formula

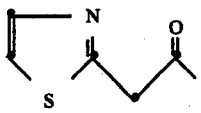

a 2-(1-tetrazolyl)acetyl group of the formula

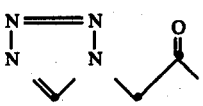

or a 2-(5-tetrazolyl)acetyl group of the formula

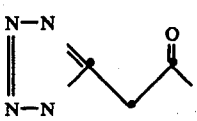

The term "substituted ammonium cation" refers to cations such as the ammonium, tetramethylammonium, tetraethylammonium, tetrabutylammonium, tributylammonium, trimethylammonium, triethylammonium, tribenzylammonium, trihexylammonium, trimethylphenylammonium, triphenylammonium, and the like.

The preferred β,γ-azetidinone sulfinic acid compounds of formula 3 produced by the process of this invention include:
N-(benzhydryl 3'-hydroxymethyl-2'-yl-2'-(R,S)-but-3'-enoate)-2-(R)-(ammonium sulfinate)-3-(S)-(p-toluylamido)-4-oxo-azetidine;
N-(benzhydryl 3'-hydroxymethyl-2'-yl-2'-(R,S)-but-3'-enoate)-2-(R)-(lithium sulfinate)-3-(S)-(p-toluylamido)-4-oxo-azetidine;

N-(lithium 3'-hydroxymethyl-2'-yl-2'-(R,S)-but-3'-enoate)-2-(R)-(lithium sulfinate)-3-(S)-(p-toluylamido)-4-oxo-azetidine;

N-(lithium 3'-hydroxymethyl-2'-yl-2'-(R,S)-but-3'-enoate)-2-(R)-(lithium sulfinate)-3-(S)-(phenoxyacetamido)-4-oxo-azetidine;

N-(benzhydryl 3'-hydroxymethyl-2'-yl-2'-(R,S)-but-3'-enoate)-2-(R)-ammonium sulfinate)-3-(S)-(phenoxyacetamido)-4-oxo-azetidine;

N-(benzhydryl 3'-hydroxymethyl-2'-yl-2'-(R,S)-but-3'-enoate)-2-(R)-(lithium sulfinate)-3-(S)-(phenylacetamido)-4-oxo-azetidine;

N-(benzhydryl 3'-hydroxymethyl-2'-yl-2'-(R,S)-but-3'-enoate)-2-(R)-(ammonium sulfinate)-3-(S)-(phenylacetamido)-4-oxo-azetidine;

N-(t-butyl 3'-hydroxymethyl-2'-yl-2'-(R,S)-but-3'-enoate)-2-(R)-(sodium sulfinate)-3-(S)-(phenylacetamido)-4-oxo-azetidine;

N-(benzhydryl 3'-hydroxymethyl-2'-yl-2'-(R,S)-but-3'-enoate)-2-(R)-(ammonium sulfinate)-3-(S)-[2-(thien-2-yl)acetamido]-4-oxo-azetidine;

N-(4-methoxybenzyl 3'-hydroxymethyl-2'-yl-2'-(R,S)-but-3'-enoate)-2-(R)-(lithium sulfinate)-3-(S)-[2-(thien-2-yl)acetamido]-4-oxo-azetidine;

N-(benzhydryl 3'-hydroxymethyl-2'-yl-2'-(R,S)-but-3'-enoate)-2-(R)-(sodium sulfinate)-3-(S)-[2-(fur-2-yl)acetamido]-4-oxo-azetidine;

N-(t-butyl 3'-hydroxymethyl-2'-yl-2'-(R,S)-but-3'-enoate)-2-(R)-(tetraethylammonium sulfinate-3-(S)-[2-(tetrazol-1-yl)acetamido]-4-oxo-azetidine;

N-(benzhydryl 3'-hydroxymethyl-2'-yl-2'-(R,S)-but-3'-enoate)-2-(R)-(sodium sulfinate)-3-(S)-(2-amino-2-phenylacetamido)-4-oxo-azetidine;

N-(tetramethylammonium 3'-hydroxymethyl-2'-yl-2'-(R,S)-but-3'-enoate)-2-(R)-(tetramethylammonium sulfinate)-3-(S)-[2-amino-2-(4-hydroxyphenyl)acetamido]-4-oxo-azetidine;

N-(triphenylammonium 3'-hydroxymethyl-2'-yl-2'-(R,S)-but-3'-enoate)-2-(R)-(triphenylammonium sulfinate)-3-(S)-[2-hydroxy-2-(3-chlorophenyl)acetamido]-4-oxo-azetidine;

N-(benzhydryl 3'-hydroxymethyl-2'-yl-2'-(R,S)-but-3'-enoate)-2-(R)-(potassium sulfinate)-3-(S)-[2-hydroxy-2-(4-hydroxyphenyl)acetamido]-4-oxo-azetidine;

N-(benzhydryl 3'-hydroxymethyl-2'-yl-2'-(R,S)-but-3'-enoate)-2-(R)-(ammonium sulfinate)-3-(S)-[D-(5-(2,4-dichlorobenzyloxycarbonylamino))-5-(benzhydryl carboxylate)valeramido]-4-oxo-azetidine;

N-[(4-methoxybenzyl) 3'-hydroxymethyl-2'-yl-2'-(R,S)-but-3'-enoate]-2-(R)-(tetraethylammonium sulfinate)-3-(S)-[D-(5-amino)-5-(4-methoxybenzyl)carboxylate)valeramido]-4-oxo-azetidine and N-(benzhydryl 3'-hydroxymethyl-2'-yl-2'-(R,S)-but-3'-enoate)-2-(R)-(tetraethylammonium sulfinate)-3-(S)-[D-(5-(2,4-dichlorobenzyloxycarbonyl))-5-(benzhydryl carboxylate)valeramido]-4-oxo-azetidine.

The more preferred β,γ-azetidinone sulfinic acid compounds of formula 3 of this invention include N-[(4-methoxybenzyl) 3'-hydroxymethyl-2'-yl-2'-(R,S)-but-3'-enoate]-2-(R)-(sodium sulfinate)-3-(S)-[D-(5-(2,4-dichlorobenzyloxycarbonylamino))-5-((4-methoxybenzyl)carboxylate)valeramido]-4-oxo-azetidine;

N-(benzhydryl 3'-hydroxymethyl-2'-yl-2'-(R,S)-but-3'-enoate)-2-(R)-(sodium sulfinate)-3-(S)-[D-(5-benzyloxycarbonylamino)-5-(benzhydryl carboxylate)valeramido]-4-oxo-azetidine;

N-[(4-methoxybenzyl) 3'-hydroxymethyl-2'-yl-2'-(R,S)-but-3'-enoate]-2-(R)-(sodium sulfinate)-3-(S)-[D-(5-(4-methoxybenzyloxycarbonylamino))-5-((4-methoxybenzyl)carboxylate)valeramido]-4-oxo-azetidine;

N-(benzhydryl 3'-hydroxymethyl-2'-yl-2'-(R,S)-but-3'-enoate)-2-(R)-(potassium sulfinate)-3-(S)-[D-(5-(2,4-dichlorobenzyloxycarbonylamino))-5-(benzhydryl carboxylate)valeramido]-4-oxo-azetidine;

N-(t-butyl 3'-hydroxymethyl-2'-yl-2'-(R,S)-but-3'-enate)-2-(R)-(sodium sulfinate)-3-(S)-[D-(5-(2,4-dichlorobenzyloxycarbonylamino))-5-((t-butyl)-carboxylate)valeramido]-4-oxo-azetidine;

N-(t-butyl 3'-hydroxymethyl-2'-yl-2'-(R,S)-but-3'-enoate)-2-(R)-(potassium sulfinate)-3-[D-(5-((4-methoxybenzyloxycarbonyl)amino)-5-((t-butyl)carboxylate)valeramido]-4-oxo-azetidine;

N-(t-butyl 3'-hydroxymethyl-2'-yl-2'-(R,S)-but-3'-enoate)-2-(R)-(sodium sulfinate)-3-(S)-(p-toluylamido)-4-oxo-azetidine;

N-[(4-methoxybenzyl) 3'-hydroxymethyl-2'-yl-2'-(R,S)-but-3'-enoate]-2-(R)-(sodium sulfinate)-3-(S)-(p-toluylamido)-4-oxo-azetidine;

N-(benzhydryl 3'-hydroxymethyl-2'-yl-2'-(R,S)-but-3'-enoate)-2-(R)-(potassium sulfinate)-3-(S)-(p-toluylamido)-4-oxo-azetidine;

N-(potassium 3'-hydroxymethyl-2'-yl-2'-(R,S)-but-3'-enoate)-2-(R)-(potassium sulfinate)-3-(S)-(p-toluylamido)-4-oxo-azetidine;

N-(potassium 3'-hydroxy-2'-yl-2'-(R,S)-but-3'-enoate)-2-(R)-(potassium sulfinate)-3-(S)-(2-phenoxyacetamido)-4-oxo-azetidine;

N-(t-butyl 3'-hydroxymethyl-2'-yl-2'-(R,S)-but-3'-enoate)-2-(R)-(sodium sulfinate)-3-(S)-(2-phenoxyacetamido)-4-oxo-azetidine;

N-[(4-methoxybenzyl) 3'-hydroxymethyl-2'-yl-2'-(R,S)-but-3'-enoate]-2-(R)-(sodium sulfinate)-3-(S)-(phenoxyacetamido)-4-oxo-azetidine;

N-[(4-methoxybenzyl) 3'-hydroxymethyl-2'-yl-2'-(R,S)-but-3'-enoate]-2-(R)-(sodium sulfinate)-3-(S)-(2-phenylacetamido)-4-oxo-azetidine;

N-(benzhydryl 3'-hydroxymethyl-2'-yl-2'-(R,S)-but-3'-enoate)-2-(R)-(potassium sulfinate)-3-(S)-(phenylacetamido)-4-oxo-axetidine;

N-(t-butyl 3'-hydroxymethyl-2'-yl-2'-(R,S)-but-3'-enoate)-2-(R)-(sodium sulfinate)-3-(S)-[2-(thien-2-yl)acetamido]-4-oxo-azetidine;

N-(benzhydryl 3'-hydroxymethyl-2'-yl-2'-(R,S)-but-3'-enoate)-2-(R)-(potassium sulfinate)-3-(S)-[2-(thien-2-yl)acetamido]-4-oxo-azetidine;

N-[(4-methoxybenzyl) 3'-hydroxymethyl-2'-yl-2'-(R,S)-but-3'-enoate]-2-(R)-(sodium sulfinate)-3-(S)-[2-(thien-2-yl)acetamido]-4-oxo-azetidine and N-(benzhydryl 3'-hydroxymethyl-2'-yl-2'-(R,S)-but-3'-enoate)-2-(R)-(tri-n-butylammonium sulfinate)-3-(S)-(p-toluylamido)-4-oxo-azetidine.

The most preferred β,γ-azetidinone sulfinic acid compounds of formula 3 of this invention include:

N-(benzhydryl 3'-hydroxymethyl-2'-yl-2'-(R,S)-but-3'-enoate)-2-(R)-(sodium sulfinate)-3-(S)-[2-(thien-2-yl)acetamido]-4-oxo-azetidine;

N-(benzhydryl 3'-hydroxymethyl-2'-yl-2'-(R,S)-but-3'-enoate)-2-(R)-(sodium sulfinate)-3-(S)-[2-(phenoxyacetamido)]-4-oxo-azetidine;

N-(benzhydryl 3'-hydroxymethyl-2'-yl-2'-(R,S)-but-3'-enoate)-2-(R)-(sodium sulfinate)-3-(S)-(2-phenacetamido)-4-oxo-azetidine;

N-(benzhydryl 3'-hydroxymethyl-2'-yl-2'-(R,S)-but-3'-enoate)-2-(R)-(sodium sulfinate)-3-(S)-[D-(5-(2,4- dichlorobenzoxycarbonylamino))-5-(benzylhydryl carboxylate)valeramido]-4-oxo-azetidine;

N-(benzhydryl 3'-hydroxymethyl-2'-yl-2'-(R,S)-but-3'-enoate)-2-(R)-(sodium sulfinate)-3-(S)-(p-toluylamido)-4-oxo-azetidine;

N-(sodium 3'-hydroxymethyl-2'-yl-2'-(R,S)-but-3'-enoate)-2-(R)-(sodium sulfinate)-3-(S)-(2-phenoxyacetamido)-4-oxo-azetidine and N-(3'-hydroxymethyl-2'-yl-2'-(R,S)-but-3'-enoic acid)-2-(R)-(sulfinic acid)-3-(S)-(p-toluylamido)-4-oxo-azetidine.

The process aspect of this invention is carried out by the conventional electrolytic cells known in the electrochemical art. This invention does not provide and does not require the use of new cells or other equipment. Some discussion of electrolytic cells will be given, however.

A typical electrolytic cell of the type used for electrolytic reductions has a cathode at which reduction takes place. The cathode is maintained at a potential which is negative with respect to the anode at which only electrolyte reactions should take place. A reference electrode is usually used, also. The reference electrode, at which no reaction should take place, supplies a reference point from which the potential of the cathode is measured. Typical and frequently-used reference electrodes are the saturated calomel electrode, the mercury/mercurous chloride electrode and the silver/silver chloride electrode. The reference electrode is electrically connected to the cathode through a conductive bridge or a porous junction.

The cells used in the instant invention are divided into compartments, so that each of the electrodes is immersed in fluid which is physically separated from the fluids of the other compartments, but is electrically connected to them.

The arrangement of electrolytic cells, the construction of electrodes, and the materials which may be effectively used as dividers are all part of the common knowledge of the electrochemical art, and are described in textbooks and journal articles. Particularly useful textbooks which may be mentioned include ORGANIC ELECTROCHEMISTRY, M. M. Baizer, Editor, Marcel Dekker, Inc., New York (1973), and "TECHNIQUE OF ELECTROORGANIC SYNTHESIS", N. L. Weinberg, Editor, John Wiley & Sons, New York, (1974).

Cathodes for use in the process of this invention are made of graphite, mercury, copper, lead, zinc, or cadimum. The preferred cathodes are mercury, zinc, and lead. The cathodes should be rather highly purified, as is normally the case in electrochemistry. The form of the electrode is not important; it may be a solid sheet, gauze or cloth, a basket of shot, or a fluidized bed of particles, with equally good results. The cathode may also be made of an inert substrate plated with the cathode metal, or it may be made in the form of a sheet of the electrode composition, wrapped with gauze of the same composition to increase the electrode area.

The anode does not participate in the reductive process, and so it may be made of any suitable substance which is not attacked by the oxidative side of the electrolytic process. Anodes are usually made of the noble metals, especially platinum, or carbon. Carbon, or the Dimentionally Stable Anode ® of Diamond Shamrock Inc. are the preferred anodes.

It is most effective to arrange the cell so that the distance between the anode and the cathode is as small as possible. The relationship is desirable in all electrolytic processes, to maximize current flow and minimize the temperature rise caused by the resistance of the fluid to the flow of the current.

The solvent used in the cathode compartment of the electrolytic cell used in this invention can be water, a polar organic solvent or a mixture of water and a water-miscible polar organic solvent. The polar organic solvent used in the process of this invention should have a high dielectric constant and should not itself contain reduceable groups such as a nitro group. Suitable polar organic solvents include dimethylformamide, acetonitrile, formamide, acetamide, N,N-dimethylacetamide, methanol, ethanol, iso-propanol, tetrahydrofuran, acetone, N-methylformamide, and benzylnitrile. Preferred polar organic solvents are methanol, dimethylformamide and water.

As was described above, certain salts are used in the catholyte solution employed in the process of this invention. Such salts are salts possessing the lithium, sodium, potassium, ammonium and substituted ammonium cation. It will be recognized by those skilled in the art that salts possessing metal cations which themselves are not reduced at the same or at a less negative potential than the potential used in the specific reaction can be employed in the catholyte. More specifically, examples of suitable metal salts for use in the process include sodium perchlorate, sodium sulfate, sodium acetate, sodium chloride, sodium iodide, potassium acetate, potassium chloride, potassium perchlorate, lithium chloride and lithium perchlorate. Suitable salts for use in the catholyte of this invention containing the ammonium cation include the simple ammonium salts such as ammonium chloride and ammonium acetate and also more complex quaternary ammonium ions such as tetramethylammonium chloride, tetraethylammonium bromide, tetraethylammonium iodide, tetrapropylammonium iodide, tetrapropylammonium perchlorate, tetrabutylammonium perchlorate, tetrabutylammonium iodide, benzyltributylammonium chloride, benzyltriethylammonium chloride, methyltributylammonium iodide and tribenzylethylammonium p-toluenesulfonate.

The appropriate salt used in the catholyte solution is one that is soluble in the aqueous and/or the organic solvents described above. The concentration of the salt in the catholyte solvent is not critical; however, it is desirable to keep the concentration as high as possible to achieve the maximum conductivity of the resulting catholyte. Preferred salts for use in the catholytes of the process of this invention include sodium perchlorate, sodium sulfate, sodium acetate, sodium chloride and lithium chloride. Suitable salts for use in non-aqueous catholytic solutions, such as sodium chloride and sodium sulfate, are well known in the electrochemical art and such suitable salts are found in ELECTROANALYTICAL CHEMISTRY, Alan J. Bard, Editor, Vol. 3, Marcel Dekker, Inc. New York, (1969) pp. 57–134.

In the process of this invention the catholyte also contains a proton source. The proton source prevents the generation of high energy anions in the catholyte and thus prevents and controls the degradation of azetidinone sulfinic acid products. For example, in the absence of a proton source the hydroxy group of the azetidinone is deprotonated to form the reactive oxyanion. The instant reduction process is a 2-electron process, and the catholyte has at least one molar equivalent of proton source per molar equivalent of the cephalosporin sulfone starting material. One skilled in the art will recognize that the minimum amount of proton source required will be increased if the starting material contains hydroxy groups in addition to the 3-hydroxymethyl group, e.g., when the starting material has a 7-(S)-(2-phenyl-2-hydroxyacetamido) group. The upper limit on the concentration of proton source is at about the point where the catholyte becomes sufficiently acidic to promote lactone formation in the cephalosporin sulfone and the azetidinone sulfinic acid product. The particular proton source used in the process will vary depending upon the solvent employed for the catholyte. For a solvent which is organic or a mixture of organic and aqueous, the proton source should be a low molecular weight carboxylic acid having a pKa between about 0 to about 5. Examples of such proton sources include acetic acid, formic acid, chloroacetic acid, dichloroacetic acid, benzoic acid, trifluoroacetic acid, and phenylthioacetic acid. Examples of proton sources which can be used when water is the catholyte solvent include acids such as hydrochloric acid and sulfuric acid. When water is used as the catholyte solvent, the procedure for introducing the proton source into the catholyte is to dissolve the catholytic salt in water to attain a pH of between about 3 and about 9, followed by dissolution of the substrate cephalosporin sulfone in the salt solution while the pH is maintained at between about 3 and about 9 by the periodic addition of a mineral acid such as hydrochloric acid or sulfuric acid.

Certain catholyte salt/proton source combinations for use in this invention are preferred. Sodium sulfate/sulfuric acid and sodium chloride/hydrochloric acid are preferred combinations.

During the process of this invention the catholyte is agitated by stirring, shaking or otherwise. It is desirable to provide sufficient agitation of the catholyte to keep the surface of the cathode thoroughly swept, so that a fresh supply of starting material is constantly supplied to the cathode.

The process of this invention is carried out in an electrolytic cell wherein the anode and cathode compartments are separated by a divider. The divider may be of any of the materials commonly used in electrochemistry for this purpose. The specially useful dividers are made from the ion exchange membranes, especially those which can pass cations. The dividers used in the majority of the experimental examples of this invention are perfluorosulfonic acid cation exchange residues sold by E. I. duPont de Nemours and Co., Wilmington, Delaware under the tradename Nafion. Specifically, either Nafion 427 (a homogeneous film 7 ml. thick of 1200 equivalent weight perfluorosulfonic resin laminated with P-12 fabric of "Teflon" TFE resin) or Nafion 480 (a homogeneous film 7 ml. thick of 1200 equivalent weight perfluorosulfonic acid resin laminated with T-216 fabric of "Teflon" TFE resin) are used. However, the dividers used in this invention are not limited to the above Nafion dividers. Dividers also may be advantageously made of finely porous substances such as ceramic membranes and sintered glass membranes. One such membrane is a micropourous frit with a porosity of 0.9 to 1.4 microns. Such porous dividers may be made permeable to ions, but not to the fluids themselves, by sealing the membranes with a conductive gel, of which a typical example is agar gel saturated with an ionic substance such as, for example, potassium sulfate. Of course, the dividers used in the process of this invention should be compatible with a solvent used in the catholyte.

Since the anode occupies a cell compartment by itself, it is immersed in a conductive fluid. If the divider is a porous membrane, it is advisable to provide an anode fluid which is compatible with catholyte, such as an aqueous solution of the mineral acid used as the proton source in the catholyte. If the cell divider is porous only to ions, then the anolyte may be any convenient conductive fluid, such as dilute aqueous solutions of ionizable salts and acid. A preferred anolyte is an aqueous solution of phosphate buffer at pH 2.3.

The potential of the cathode, or the potential between the cathode and the anode, may be controlled in various ways. The most effective and precise way to control the potential is by use of a reference electrode, with its junction to the catholyte placed as physically close as possible to the cathode. The desired potential for the process is determined from the examination of a voltammogram of the system, and the potential between the cathode and the anode is adjusted to give the desired constant potential between the reference electrode and the cathode. This method of control is much more effective than control by the overall voltage between the cathode and the anode, since such voltage depends on the condition of the dividing membrane, concentration of the proton source and the catholyte as well as the concentration of the compound to be reduced in the catholyte.

Similarly, it is relatively inefficient to control the reduction by means of a current flow between the anode and the cathode, because the current flow is directly dependent on the concentration of the compound to be reduced, as well as upon the physical condition of the electrodes and of the divider. However, when an individual reduction has been thoroughly studied and the relationship between current, time and concentration is known, controlled-current electrolysis can be used for the production of repeated batches.

Thus, control of the reduction is best achieved by control of the potential between the reference electrode and the cathode or control of the current between the anode and the cathode. This control is best provided by an automatic instrument which constantly senses that potential or current and adjusts the voltage between the cathode and anode accordingly. Such instruments are available from commercial suppliers; for example, Princeton Applied Research, Inc., Princeton, N.J., U.S.A. supplies the PAR model 173 potentiostat/galvanostat.

As has been briefly discussed above, the potential for operating the process of this invention with any given combination of electrodes, catholyte and compound is determined according to the routine method of the electrochemical art, i.e. by running a voltammogram of the system. In general, a voltammogram is run on the system first in the absence of starting material to determine the hydrogen production or background wave, followed by a voltammogram in the presence of starting material, the cephalosporin sulfone. It has been found in performing voltammograms in the above manner under various conditions and with differing starting materials encompassed by this invention that the starting material reduction wave and the background wave are not sufficiently different in potential so as to operate at the current plateau in the starting material reduction wave without producing an undesirably large amount of hydrogen, i.e. an inefficient use of current. Indeed, it is frequently impossible to find a current plateau in the reduction wave of the starting material due to the plateau being obliterated by the background wave. Hence, it is necessary to examine the above initial voltammograms in order to select the potential where the fastest rate of reduction will occur while at the same time manifesting a highly efficient use of the current. In selecting this potential, it will be understood that some hydrogen production will most probably accompany the reduction, as applicant does not mean to imply that a desirable potential for the reduction is one where no hydrogen is produced.

It is not possible to specify a priori a precise potential range for the operation of the instant process with respect to a particular substrate and conditions, since the potential for every system will necessarily vary. It has been observed, however, that the potential of the cathode for reductions according to this process is from about −1.0 volt to about −1.9 volts, relative to a saturated calomel reference electrode. The highest negative potential usable for this process would be at the degradation potential of the solvent.

The reduction of this invention appears to be a 2-electron process, and so the reduction of a gram-mole of compound requires 192,974 coulombs. The length of time necessary to pass this amount of current necessarily depends upon the overall resistance of the cell, the effective area of the electrodes and the degree of agitation.

When the reduction is run in a constant potential fashion, typically the progress of the reaction is followed in at least one of the following ways: the number of amperes passed as a function of time is plotted, in order to approximately determine when the theoretically required number of coulombs has passed for completion of the reaction; or, more typically, the catholyte is periodically analyzed by high performance liquid chromatography to determine the amount of starting material and/or product that is present.

When the instant reduction process is conducted in a constant current fashion, the level of current used is chosen so as to give a fast reduction with high current efficiency. A preferred range for the constant current method is between about 2 to about 200 ma/cm$^2$.

The primary method for following the progress of a constant current reduction is high performance liquid chromatography analysis of the catholyte. Of course, when constant current conditions are used, as the concentration of starting material declines the potential will increase. Therefore, it is necessary to monitor the potential over time and adjust it accordingly to prevent substantial amounts of hydrogen production. An additional way to predict the length of time the reduction should take at a constant current level is by simply figuring the amount of time necessary to pass the theoretically required amount of coulombs for the reduction at the specific cephaolsporin sulfone starting material actually used.

The electrolytic reduction process of this invention is carried out at a temperature from above the freezing point of the liquid medium used to about 40° C., with the preferred temperature range being between about −10° C. to about 10° C.

During the instant process it is desirable to purge oxygen from the cell by passing an inert gas such as argon through the catholyte. While not essential in the process, purging of oxygen enhances the efficiency of the reduction by preventing the consumption of colombs by the reduction of any oxygen present.

As noted above, the electrolytic reduction of this invention produces both of the two possible C-2′ stereoisomers of the azetidinone sulfinic acid compounds. The ratio in which these isomers are produced is difficult to predict, since it is dependent upon the choice of electrolyte salt, solvent, concentration of the starting material, potential and temperature.

The concentration of the cephalosporin sulfone in the catholyte is widely variable and is limited only by the solubility of the compound in the catholyte. Of course, it is most economical to use relatively high concentrations, in order to obtain the maximum effectiveness from the solvents used in the process. However, work-up of the catholyte and isolation of the product is frequently more difficult when high concentrations of starting material are used.

Exemplary cephalosporin sulfone starting materials for this process include:

benzhydryl 7-(S)-[2-(thien-2-yl)acetamido]-3-hydroxymethyl-3-cephem-4-carboxylate;

benzhydryl 7-(S)-(phenoxyacetamido)-3-hydroxymethyl-3-cephem-4-carboxylate;

benzhydryl 7-(S)-(phenylacetamido)-3-hydroxymethyl-3-cephem-4-carboxylate;

benzhydryl 7-(S)-[D-(5-(2,4-dichlorobenzyloxycarbonylamino))-5-(benzhydryl carboxylate)-valeramido]-3-hydroxymethyl-3-cephem-4-carboxylate;

benzhydryl 7-(S)-(p-toluylamido)-3-hydroxymethyl-3-cephem-4-carboxylate;

sodium 7-(S)-(phenoxyacetamido)-3-hydroxymethyl-3-cephem-4-carboxylate;

sodium 7-(S)-(p-toluylamido)-3-hydroxymethyl-3-cephem-4-carboxylate;

4-methoxybenzyl 7-(S)-[D-(5-(2,4-dichlorobenzyloxycarbonylamino))-5-((4-methoxybenzyl)carboxylate)valeramido]-3-hydroxymethyl-3-cephem-4-carboxylate;

benzhydryl 7-(S)-[D-(5-(benzyloxycarbonylamino))-5-(benzhydryl carboxylate)valeramido]-3-hydroxymethyl-3-hydroxymethyl-3-cephem-4-carboxylate;

4-methoxybenzyl 7-(S)-[D-(5-(4-methoxybenzyloxycarbonylamino))-5-((4-methoxybenzyl)carboxylate)-valeramido]-3-hydroxymethyl-3-cephem-4-carboxylate;

t-butyl 7-(S)-[D-(5-(2,4-dichlorobenzyloxycarbonylamino))-5-((t-butyl)carboxylate)valeramido]-3-hydroxymethyl-3-cephem-4-carboxylate;

t-butyl 7-(S)-[D-(5-((4-methoxybenzyloxycarbonyl)amino)-5-((t-butyl)carboxylate)valeramido]-3-hydroxymethyl-3-cephem-4-carboxylate;

t-butyl 7-(S)-(p-toluylamido)-3-hydroxymethyl-3-cephem-4-carboxylate;

4-methoxybenzyl 7-(S)-(p-toluylamido)-3-hydroxymethyl-3-cephem-4-carboxylate;

potassium 7-(S)-(p-toluylamido)-3-hydroxymethyl-3-cephem-4-carboxylate;

potassium 7-(S)-(phenoxyacetamido)-3-hydroxymethyl-3-cephem-4-carboxylate;

t-butyl 7-(S)-(phenoxyacetamido)-3-hydroxymethyl-3-cephem-4-carboxylate;

4-methoxybenzyl 7-(S)-(phenoxyacetamido)-3-hydroxymethyl-3-cephem-4-carboxylate;

4-methoxybenzyl 7-(S)-(phenylacetamido)-3-hydroxymethyl-3-cephem-4-carboxylate;

t-butyl-7-(S)-[2-(thien-2-yl)acetamido]-3-hydroxymethyl-3-cephem-4-carboxylate and 4-methoxybenzyl 7-(S)-[2-(thien-2-yl)acetamido]-3-hydroxymethyl-3-cephem-4-carboxylate.

The carboxy groups of the starting materials should be protected in the electrolysis process for synthesizing the azetidinone sulfinic acid compounds when an organic solvent or an organic solvent plus water is used. The use of carboxy protecting groups is limited to ones that are stable to the electrolysis process (i.e., not easily reduced) thus ruling out protecting groups such as p-nitrobenzyl, 2,2,2-trichloroethyl, 2,2,2-tribromoethyl, 2,2-dibromoethyl, 2-iodoethyl, 2,2-diiodomethyl, 2,2,2-triiodomethyl, and like protecting groups having nitro, activated halogeno or cyano substituents. Likewise, the carboxy protecting groups used are stable under the acidic conditions created by the proton source used with all of the solvents of this process. Acid-labile protecting groups, for example the tri-alkylsilyl groups such as trimethylsilyl, should be avoided. If these limitations are heeded, protecting groups that can be used in the present invention where the term "protected carboxy" is specified are commonly used carboxylic acid protecting groups such as tert-butyl, benzyl, diphenylmethyl (benzhydryl), 4-methoxybenzyl, $C_2$–$C_6$ alkanoyloxymethyl, phenacyl, para-chlorophenylacyl, dimethylallyl, and the like. Preferred carboxylic acid protecting groups are benzhydryl, 4-methoxybenzyl and tert-butyl.

It is not essential that amino groups present in the starting material be protected during the electrolysis process of the invention. However, if left unprotected, any such free amino groups can undergo salt formation with the acid serving as the proton source. Accordingly, in such instances the amount of the proton source consumed by free amino groups is compensated for by adding additional proton source as required by the conditions for the particular electrolysis. If an amino-protecting group is used, it is again necessary, as with carboxylic acid protecting groups, to avoid the use of groups possessing easily reduceable substitutents, e.g. the 4-nitrobenzyloxycarbonyl group, 2,2,2-trichloroethoxycarbonyl, the β-haloethyloxycarbonyls, etc. As with the carboxylic acid groups, it is desirable to avoid amino protecting groups which are acid-labile with regard to the proton source employed, not because of the resulting degradation of the molecular, but due to the removal of the protecting group and therefore the presence of extra species in solution possibly complicating the isolation procedure. With these limitations in mind, the protecting groups that can be used in situations where "protected amino" groups are specified are those known in the cephalosporin art such as the benzyloxycarbonyl group, the 2,4-dichlorobenzyloxycarbonyl group, and the 4-methoxybenzyloxycarbonyl. In some instances, the major reason for protecting an amino group of the starting materials in the instant process is to provide that the product of the process is in protected form for conversion to antibacterial compounds via the reactions discussed below. By protecting the amino groups before the electrolysis, the azetidinone sulfinic acid products can be used in the ensuing reactions with a minimum of handling.

In the foregoing definitions, amino and carboxy protecting groups are not exhaustively defined. Many such protecting groups are well known in the art and the use of other groups equally applicable to the process and compounds, such as those described in Theodora W. Greene, "PROTECTIVE GROUPS IN ORGANIC SYNTHESIS", John Wiley & Sons, 1981, New York, will be recognized as suitable. Thus, there is no novelty or inventiveness asserted with regard to the "protecting groups" in this specification.

A typical work-up procedure following the reduction process of this invention is as follows: the catholyte is removed from the cathode compartment, and is diluted with a 1:1 0.3 M pH 7 phosphate:saturated sodium chloride solution. The solution is extracted with ethyl acetate, and the extracts are washed with the above phosphate:sodium chloride buffer. The ethyl acetate extracts are dried over magnesium sulfate, filtered, the ethyl acetate is removed and the resultant foam is purified by high performance liquid chromatography.

An alternative procedure, used for the isolation of the azetidinone sulfinic acid in the form of a carboxylic acid salt, is as follows. The catholyte is removed from the cathode compartment and is diluted with ethyl acetate. Sulfuric acid (12N) is then added until the pH of the aqueous layer is 1.5. The ethyl acetate layer is separated, evaporated and the resultant foam is taken up again in ethyl acetate and recrystallized.

Finally, if there is no desire to isolate the product azetidinone sulfinic acid compounds, the catholyte can be removed from the cathode compartment and used as is in the oxidation steps for conversion of the product to antibacterial compounds as described below.

The β,γ-azetidinone sulfinic acid compounds of this invention are useful in the preparation of known epioxazoline compound according to the following Scheme 1:

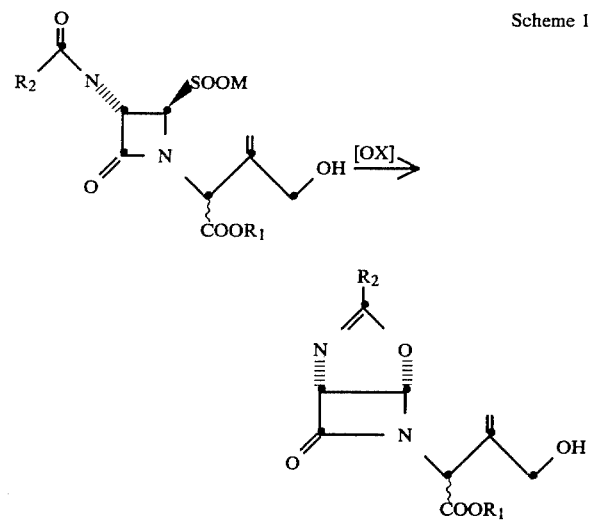

Scheme 1

This conversion is carried out by the reaction of the azetidinone sulfinic acid compounds with an oxidizing agent. The reaction generally is carried out by mixing from between at least one molar equivalent and about 1.5 molar equivalents of the oxidizing agent with each molar equivalent of the azetidinone sulfinic acid compound. An even larger excess of the oxidizing agent can be employed; however, no advantage is gained thereby. Preferably, therefore, the ratio of reactants is from about 1.0 to about 1.1 molar equivalents of oxidizing agent per molar equivalent of the axetidinone sulfinic acid compound. Preferably, the resulting mixture is dissolved in a suitable inert organic solvent and this reaction mixture is maintained at a temperature from about 0° C. to about 30° C., for a period sufficient for the completion of the reaction. This oxidation reaction can be carried out on an azetidinone sulfinic acid compound that has been isolated and/or purified, or the oxidizing agent can be added directly to the catholyte after it has been removed from the cathode compartment.

The term "inert organic solvent" means an organic solvent which, under the conditions of the epi-oxazoline formation, does not appreciably react either with the reactants or with the products. Suitable inert organic solvents include, for example, aromatic hydrocarbons, such as benzene, toluene, ethylbenzene, cumene, and the like; halogenated hydrocarbons, such as carbon tetrachloride, chlorobenzene, bromoform, bromobenzene, methylene chloride, ethylene chloride, 1,1,2-trichloroethane, ethylene dibromide, and the like; amides, such as N,N-dimethylformamide, and the like; alcohols, such as methanol, ethanol, and the like; esters, such as ethyl acetate, and the like; nitriles, such as acetonitrile, and the like; and the other appropriate inert solvents. Preferred solvents include N,N-dimethylformamide, acetonitrile, ethylacetate, methylene chloride, and the like.

The oxidizing agent used in this reaction can be any of a wide range of such agents. Typical agents include, for example, lead (IV) compounds such as lead tetraacetate, lead oxide, and the like; manganese (IV) compounds, such as manganese acetoacetonate, manganese oxide, and the like; sodium hypochlorite; N-haloimides, such as N-bromosuccinimide, and the like; ammonium cerium nitrate; and other like compounds. Preferably, the oxidizing agent is a lead (IV) compound, in particular, lead tetraacetate, or an N-bromoimide, in particular, N-bromosuccinimide.

The temperature of the oxidation reaction generally is from about 0° C. to about 30° C. Preferably, the reaction temperature is at the lower end of this range, generally from about 0° C. to about 5° C.

Typically the oxidation reaction is complete in a very short time, generally a matter of a few minutes. However, the time of the reaction can be greatly extended, for example, to several hours, without detrimental effects. Normally the time of the reaction will be no longer than about 1 hour.

The above oxidation reaction is described and claimed in W. A. Spitzer, U.S. application Ser. No. 442,052, filed this even date.

As noted above, the epi-oxazolines of the formula

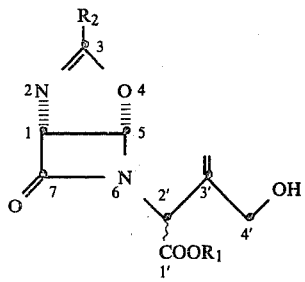

produced by the oxidation of the azetidinone sulfinic acid compounds of this invention, are useful as intermediates in the production of antibiotically active compounds. Specifically, the epi-oxazolines are useful in the preparation of oxygen analogs of cephalosporins, as described in U.S. Pat. Nos. 4,220,766, 4,271,295 and 4,271,296 herein incorporated by reference.

The $\beta$, $\gamma$-azetidinone sulfinic acid compounds wherein the C-3 substituent is a carbamato side chain, i.e., an azetidinone sulfinic acid compound of the formula

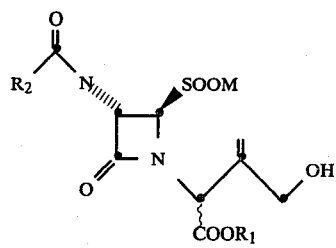

wherein $R_2$ is $C_1$-$C_6$ alkoxy, $C_3$-$C_6$ cycloalkyloxy, benzyloxy, or substituted benzyloxy, with the substituents are one to three groups chosen from the group consisting of $C_1$-$C_4$ alkyl, $C_1$-$C_4$ alkoxy or chloro; are useful intermediates for 1-oxa-$\beta$-lactam antibiotics. The above azetidinone sulfinic acid is reacted with lead tetraacetate in liquid sulfur dioxide containing copper (II) ion to provide an isomeric mixture of a cyclization product, i.e., a 3-exomethylene 1-oxa $\beta$-lactam compound of the formula

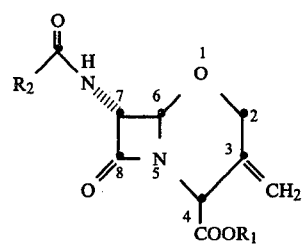

and a 3-methyl 1-oxa $\beta$-lactam compound of the formula

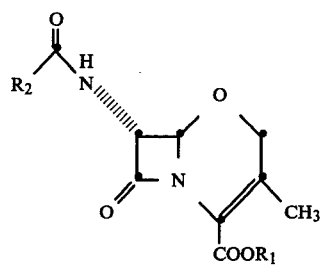

wherein the C-7 group is also a carbamato group as defined for the starting azetidinone sulfinic acid. This process proceeds without production of the epioxazoline compound, and is carried out in an inert organic solvent at a temperature between about $-25°$ C. to about 0° C. with between about 1.0 to about 2.5 molar equivalents of lead tetraacetate per molar equivalent of azetidinone sulfinic acid compound starting material.

The amount of sulfur dioxide used can be between about 1 to about 3 molar equivalents per molar equivalent of substrate azetidinone compound, preferably in excess of the molar equivalents of substrate compound used. The sulfur dioxide can be used as a solvent by itself or in addition to an inert organic solvent such as ethyl acetate, methylene chloride, tetrahydrofuran, dioxane, and the like.

Copper (II) ion is readily available as copper sulfate, employing between about 10 to about 15 mg of copper sulfate per millimole of starting material.

A preferred procedure for the above cyclization to a 1-oxa compound comprises adding lead tetraacetate and copper sulfate in liquid sulfur dioxide, and stirring the resultant mixture for from 20 to 30 minutes.

Alternatively, the reaction can be carried out in an inert organic solvent using lead tetraacetate without the presence of sulfur dioxide or copper (II).

The 3-exomethylene 1-oxa β-lactam compound can be easily isomerized to the 3-methyl 1-oxa β-lactam compound in the presence of a base such as triethylamine. The 3-methyl-1-oxa β-lactam compounds are intermediates in the synthesis of 1-oxa β-lactam antibiotic compounds, such as those described in U.S. Pat. Nos. 4,138,486 and 4,226,866.

The details for the above cyclization reaction of the azetidinone sulfinic acid compound to the 1-oxa β-lactam intermediates are described in co-pending U.S. application Ser. No. 442,080, filed this even date. The conversion of the 1-oxa β-lactam intermediate produced in this cyclization process to the 1-oxa β-lactam antibiotic compounds is described in the above co-pending U.S. application and U.S. Pat. Nos. 4,226,866 and 4,138,486, said patents herein corporated by reference.

The 2',3',-double bond ("α,β")azetidinone sulfinic acid compounds of this invention have the general formula 2

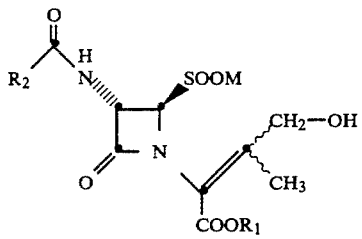

are referred to as the "α,β sulfinic acids". This invention encompasses both isomeric forms of the compounds: the 2'-Z isomer represented by the partial formula

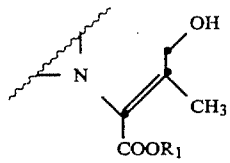

and the 2'-E isomer, represented by the partial formula

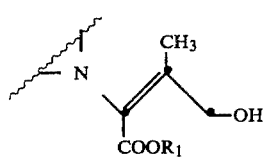

As with the β,γ sulfinic acids discussed above, the α,β sulfinic acids claimed in this invention have the 2-(R) (carbon with the sulfinic acid function bonded to it) and the 3-(S) (carbon with the acylamido group bonded to it) configuration, these configurations being necessary for the formation of the epi-oxazoline compounds required for the conversion of these α,β azetidinones sulfinic acids to antibiotic compounds, as discussed below.

As used in regard to the α,β azetidinone sulfinic acid compounds of this invention, represented by the above formula 2, $R_2$ is 1,4-cyclohexadienyl, phenyl or substituted phenyl, wherein the substituents are one or two groups chosen from the group consisting of chlorine, bromine, hydroxy, trifluoromethyl, $C_1$ to $C_4$ alkyl, $C_1$ to $C_4$ alkoxy, carboxy, carboxymethyl, hydroxymethyl, aminomethyl and protected aminomethyl. The symbols M and $R_1$ have the same meaning for the α,β sulfinic acid compounds as they do for the β,γ sulfinic acid compounds.

Exemplary α,β sulfinic acid compounds of formula 2 of this invention include:

N-(benzhydryl 3'-hydroxymethyl-2'-yl-but-2'-(E,Z)-enoate)-2-(R)-tetraethylammonium sulfinate)-3-(S)-(4-chlorobenzamido)-4-oxo-azetidine;

N-(benzhydryl 3'-hydroxymethyl-2'-yl-but-2'-(E,Z)-enoate)-2-(R)-(sodium sulfinate)-3-(S)-(3,4-dichlorobenzamido)-4-oxo-azetidine;

N-(t-butyl 3'-hydroxymethyl-2'-yl-but-2'-(E,Z)-enoate)-2-(R)-(potassium sulfinate)-3-(S)-(3-bromobenzamido)-4-oxo-azetidine;

N-(benzhydryl 3'-hydroxymethyl-2'-yl-but-2'-(E,Z)-enoate)-2-(R)-(ammonium sulfinate)-3-(S)-(4-hydroxybenzamido)-4-oxo-azetidine;

N-[(4-methoxybenzyl) 3'-hydroxymethyl-2'-yl-but-2-(E,Z)-enoate]-2-(R)-(sodium sulfinate)-3-(S)-(2,4-dimethylbenzamido)-4-oxo-azetidine;

N-(lithium 3'-hydroxymethyl-2'-yl-but-2'-(E,Z)-enoate)-2-(R)-(lithium sulfinate)-3-(S)-(4-ethylbenzamido)-4-oxo-azetidine;

N-(potassium 3'-hydroxymethyl-2'-yl-but-2'-(E,Z)-enoate)-2-(R)-(potassium sulfinate)-3-(S)-(3-n-propyl-benzamido)-4-oxo-azetidine;

N(tri-n-butylammonium 3'-hydroxymethyl-2'-yl-but-2'-(E,Z)-enoate)-2-(R)-(tri-n-butylammonium sulfinate)-3-(S)-(3-trifluoromethylbenzamido)-4-oxo-azetidine;

N-(tetraethylammonium3'-hydroxymethyl-2'-yl-but-2'-(E,Z)-enoate)-2-(R)-(tetraethylammonium sulfinate)-3-(S)-(4-trifluoromethylbenzamido)-4-oxo-azetidine;

N-(benzhydryl 3'-hydroxymethyl-2'-yl-but-2'-(E,Z)-enoate)-2-(R)-(triphenylammonium sulfinate)-3-(S)-(4-carboxybenzamido)-4-oxo-azetidine;

N-(sodium 3'-hydroxymethyl-2'-yl-but-2'-(E,Z)-enoate)-2-(R)-sodium sulfinate)-3-(S)-[2-(carboxymethyl)benzamido]4-oxo-azetidine;

N-(tri-n-butylammonium 3'-hydroxymethyl-2'-yl-but-2'-(E,Z)-enoate-2-(R)-(tri n-butylammonium sulfinate)-3-(S)-[2-(hydroxymethyl)benzamido]-4-oxo-azetidine;

N-(benzhydryl 3'-hydroxymethyl-2'-yl-but-2'-(E,Z)-enoate)-2-(R)-(tri-n-butylammonium sulfinate)-3-(S)-[3-(hydroxymethyl)benzamido]-4-oxo-azetidine;

N(benzhydryl 3'-hydroxymethyl-2'-yl-but-2'-(E,Z)-enoate)-2-(R)-(sodium sulfinate)-3-(S)-[4-(aminomethyl)benzamido]-4-oxo-azetidine;

N-(t-butyl 3'-hydroxymethyl-2'-yl-but-2'-(E,Z)-enoate)-2-(R)-(tri-n-butylammonium sulfinate)-3-(S)-[2-(aminomethyl)benzamido]-4-oxo-azetidine;

N-[(4-methoxybenzyl) 3'-hydroxymethyl-2'-yl-but-2'-(E,Z)-enoate]-2-(R)-(potassium sulfinate)-3-(S)-(3-methyl-4-hydroxybenzamido)-4-oxo-azetidine;

N-(benzhydryl 3'-hydroxymethyl-2'-yl-but-2'-(E,Z)-enoate)-2-(R)-(sodium sulfinate)-3-(S)-(4-ethyl-2-hydroxybenzamido)-4-oxo-azetidine;

N-(benzhydryl 3'-hydroxymethyl-2'-yl-but-2'-(E,Z)-enoate)-2-(R)-(tri-n-butylammonium sulfinate)-3-(S)-[2-(aminomethyl)-4-(hydroxymethyl)benzamido]-4-oxo-azetidine;

N-(benzhydryl 3'-hydroxymethyl-2'-yl-but-2'-(E,Z)-enoate)-2-(R)-(sodium sulfinate)-3-(S)-(2-hydroxy-4-chlorobenzamido)-4-oxo-azetidine;

N-(benzhydryl 3'-hydroxymethyl-2'-yl-but-2'-(E,Z)-enoate)-2-(R)-(tri-n-butylammonium sulfinate)-3-(S)-[4-(carboxyethyl)-2-methylbenzamido]-4-oxo-azetidine.

The preferred α,β compounds of formula 2 of this invention are:

N-(benzhydryl 3'-hydroxymethyl-2'-yl-but-2'-(E,Z)-enoate)-2-(R)-sodium sulfinate)-3-(S)-(p-toluylamido)-4-oxo-azetidine and N-(benzhydryl 3'-hydroxymethyl-2'-yl-but-2'-(E,Z)-enoate)-2-(R)-tri-n-butylammonium sulfinate)-3-(S)-(p-toluylamido)-4-oxo-azetidine.

The above α,β sulfinic acis are minor products in the electrolytic process of this invention described above for the preparation of the β,γ sulfinic acid compounds. The isomerization of the double bond from the β,γ positions to the α,β position is caused by basic species occurring in the catholyte and/or the work-up procedure. In this regard, the catholyte salt used is especially effective in catalyzing the isomerization of the double bond, and in particular the tri-n-butylammonium para-toluenesulfonate salt has been found to give the largest amount of the α,β sulfinic acid isomer. A specific set of reaction conditions for the electrolysis process of this invention that will produce the ⊕,β sulfinic acid isomer exclusively involves the use of methanol as the solvent, acetic acid as the proton source, tri-n-butylammonium para-toluenesuflonate as the catholyte salt with the temperature of the reaction between about −10° C. to about 10° C. In a specific embodiment of this process, benzhydryl 7-(S)-(p-toluylamido)-3-hydryl 7-(S)-(p-toluylamido)-3-hydroxymethyl-3-cephem-4-carboxylate sulfone is electrolytically reduced to give N-(benzhydryl 3'-hydroxymethyl-2'-yl-but-2'-(E,Z)-enoate)-2-(R)-(tri-n-butylammonium sulfinate)-3-(S)-(p-toluylamido)-4-oxoazetidine.

The preferred cephalosporin sulfone starting materials for the instant process include:

benzhydryl 7-(S)-(4-chlorobenzamido)-3-hydroxymethyl-3-cephem-4-carboxylate;

benzhydryl 7-(S)-(3,4-dichlorobenzamido)-3-hydroxymethyl-3-cephem-4-carboxylate;

t-butyl 7-(S)-(3-bromobenzamido)-3-hydroxymethyl-3-cephem-4-carboxylate;

benzhydryl 7-(S)-(4-hydroxybenzamido)-3-hydroxymethyl-3-cephem-4-carboxylate;

4-methoxybenzyl 7-(S)-(2,4-dimethylbenzamido)-3-hydroxymethyl-3-cephem-4-carboxylate;

lithium 7-(S)-(4-ethylbenzamido)-3-hydroxymethyl-3-cephem-4-carboxylate;

potassium 7-(S)-[3-(n-propyl)benzamido]-3-hydroxymethyl-3-cephem-4-carboxylate;

tri-n-butylammonium 7-(S)-(3-trifluoromethylbenzamido)-3-hydroxymethyl-3-cephem-4-carboxylate;

tetraethylammonium 7-(S)-(4-trifluoromethylbenzamido)-3-hydroxymethyl-3-cephem-4-carboxylate;

benzhydryl 7-(S)-(4-carboxybenzamido)-3-hydroxymethyl-3-cephem-4-carboxylate;

sodium 7-(S)-[2-(carboxymethyl)benzamido]-3-hydroxymethyl-3-cephem-4-carboxylate;

tri-n-butylammonium 7-(S)-[2-(hydroxymethyl)-benzamido]-3-hydroxymethyl-3-cephem-4-carboxylate;

benzhydryl 7-(S)-[3-(hydroxymethyl)benzamido]-3-hydroxymethyl-3-cephem-4-carboxylate;

benzhydryl 7-(S)-[4-(aminomethyl)benzamido]-3-hydroxymethyl-3-cephem-4-carboxylate;

t-butyl 7-(S)-[2-(aminomethyl)benzamido]-3-hydroxymethyl-3-cephem-4-carboxylate;

4-methoxybenzyl 7-(S)-(3-methyl-4-hydroxybenzamido)-3-hydroxymethyl-3-cephem-4-carboxylate;

benzhydryl 7-(S)-(4-ethyl-2-hydroxybenzamido)-3-hydroxymethyl-3-cephem-4-carboxylate;

benzhydryl 7-(S)-[2-(aminomethyl)-4-(hydroxymethyl)benzamido]-3-hydroxymethyl-3-cephem-4-carboxylate;

benzhydryl 7-(S)-(2-hydroxy-4-chlorobenzamido)-3-hydroxymethyl-3-cephem-4-carboxylate;

benzhydryl 7-(S)-[4-(carboxyethyl)-2-methylbenzamido]-3-hydroxymethyl-3-cephem-4-carboxylate and benzhydryl 7-(S)-(p-toluylamido)-3-hydroxymethyl-3-cephem-4-carboxylate.

The α,β azetidine sulfinic acids discussed above are converted to the corresponding α,β-unsaturated epi-oxazoline of the formula

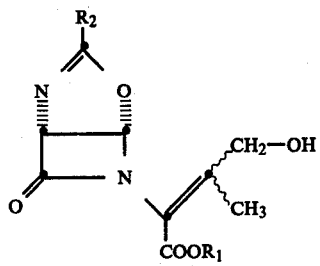

by the same process described above for the conversion of the β,γ sulfinic acid compounds. In the above formula for the α,β epi-oxazoline compounds, $R_2$ and $R_1$ are the same as for the corresponding α,β sulfinic acids, as discussed above. These α,β epi-oxazoline compounds are then converted to 1-oxa β-lactam antibacterial compounds using the same processes as described for the β,γ epi-oxazoline compounds, as discussed above.

7-(S)-acylamino-3-hydroxymethyl cephalosporin sulfones employed in the electrolysis to provide the azetidinone sulfinic acids are obtained from 7-(R)-acylamino cephalosporanic acids. A cephalosporanic acid (3-acetoxymethyl-3-cephem) is first oxidized to the corresponding sulfone and the 7-(R)-acylamino side chain of the sulfone is epimerized to the 7-(S)-acylamino sulfone. The epimeric sulfone acid is then deacetylated at the 3' position to provide the 7-(S)-acylamino-3-hydroxymethyl-3-cephem-4-carboxylic acid sulfone.

The above sequence of reactions is illustrated by the following reaction scheme.

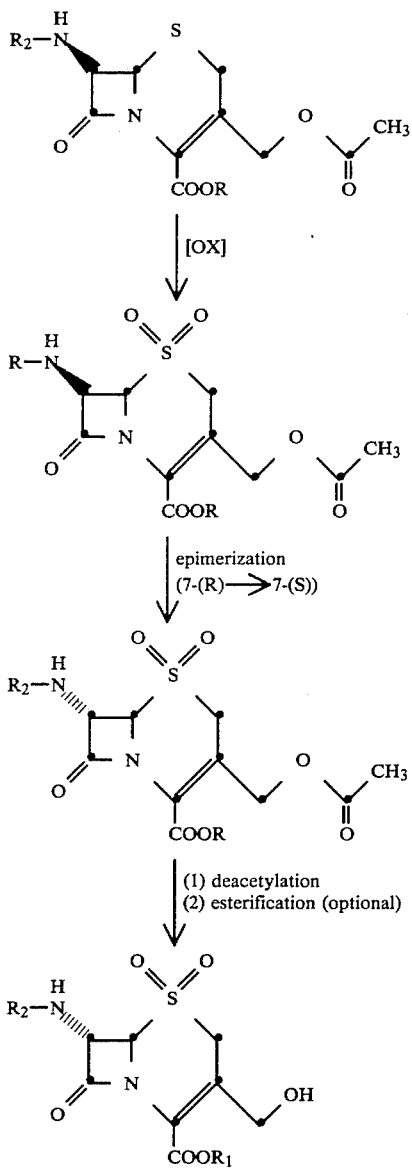

In the above formulas, $R_1$ and $R_2$ are as defined for formula 1, and R is hydrogen, an acid salt or a carboxy protecting group.

The preparation of the cephalosporin sulfone is best carried out in an aqueous reaction medium maintained at a pH between about 5.0 and about 6.0 with an excess of potassium hydrogen persulfate. The oxidation proceeds well at temperatures between about 15° C. to about 45° C. The sulfone is recovered from the aqueous reaction medium by acidifying the mixture to form the free sulfone carboxylic acid and extraction of the latter with a suitable water immiscible solvent such as ethyl acetate. This process is more thoroughly described in copending application Ser. No. 442,079, filed this even date.

The epimerization of the sulfone free acid is preferably carried in an aqueous medium as follows. A slurry of the sulfone free acid in water is treated with an aqueous solution of sodium acetate containing at least an equal molar amount of sodium acetate. An aqueous solution of piperazine is then added dropwise until the pH of the solution is between about 9.5 to about 10. After the pH is adjusted, the epimerization mixture is stirred for about 5 to 15 minutes. Ethyl acetate is added to the mixture which is then acidified to a pH of about 2.0 with concentrated hydrochloric acid. The epimeric sulfone free acid is then extracted with ethyl acetate. This process is more fully described in copending U.S. application Ser. No. 442,077, filed this even date.

The epimerization product, the 7-(S)-acylamino cephalosporanic acid sulfone, is then deacylated with immobilized citrus acetylesterase to provide the 7-(S)-acylamino-3-hydroxymethyl cephalosporin sulfone.

The deacylation is preferably carried out with the esterase immobilized on a modified silica gel. This modified silica gel is prepared using silica gel of 70-230 mesh and 62-200μ particle size (i.e. Fractosil 200, E. Merck and Co.). The silica gel is prepared by first deaerating a slurry of the silica in aqueous 10% nitric acid, heating the acidic slurry for 3 hours at about 80° C. and then rinsing with water. The clean silica gel was then slurried in 10% 3-aminopropyltriethoxysilane and the slurry deaerated under vacuum. The pH is adjusted to between 3 and 4 with dilute hydrochloric acid and the slurry agitated periodically with heating at 80° C. for 3 hours. This modified silica is collected by filtration, washed with water, and dried for 16 hours at 105° C. The dried modified silica is slurried with an aqueous 3% solution of glutaraldehyde buffered by pH 7 phosphate (5-10 vol/wt. of silica). The slurry is periodically agitated during 3 hours and is then washed with water and pH 7 citrate buffer.

A neutral aqueous solution of the citrus acetylesterase is added to the aldehyde-silica and allowed to interact for about 20 hours. The silicaenzyme complex is then transfered to a glass column and washed with pH 7 citric acid buffer.

The sulfone is dissolved in 0.2 M aqueous sodium citrate and the pH of the solution is adjusted to 7 with 1 M sodium hydroxide. The solution is then passed over the silica-enzyme column. Ethyl acetate is added to the effluent and the mixture is chilled to 0° C. The pH of the cold mixture is adjusted to 2.5 with hydrochloric acid and the ethyl acetate layer is separated. The acidified aqueous phase is extracted further with ethyl acetate and all extracts are combined and washed with acidified brine and dried.

The resultant 7-(S)-acylamino-3-hydroxymethyl-3-cephem-4-carboxylic acid sulfone is recovered from the ethyl acetate by evaporation.

The deacylated sulfone may also be recovered as the carboxylic acid salt by adding sodium 2-ethylhexanoate to the combined ethyl acetate extracts or alternatively changing solvents from ethyl acetate to methanol and adding sodium acetate. As another alternative, washed and dried extract is concentrated in vacuo and the concentrate of the 3-hydroxymethyl sulfone is esterified. For example, the concentrate can be treated with diphenyldiazomethane to form diphenylmethyl 7-(S)-acylamino-3-hydroxymethyl-3-cephem-4-carboxylate sulfone. As noted above in the description of the electrolysis process of this invention, the esterification of the C-4 carboxy group prior to the reduction is an optional reaction when water is the solvent.

Preferably, the esterification of the 3-hydroxymethyl sulfone acid is carried out by adding ethyl acetate containing a stoichiometric amount of diphenyldiazomethane to the effluent of the column. The 3-hydroxymethylsulfone benzhydryl ester is recovered rather than first recovering the free acid and then esterifying.

This preferred route of esterification diminishes the amount of lactone formed with the 3-hydroxymethyl group and the free carboxy group by intramolecular esterification. This deacetylation process using an immobilized enzyme is further described in copending U.S. application Ser. No. 442,078, filed this even date.

In the following examples, the electrolysis apparatus consisted of a mercury pooly cathode (unless specified otherwise) having an area of approximately 20 cm². Additionally, the cathode compartment is fitted with a dearerating frit, a magnetic stir bar and a saturated calomel reference electrode. The cathode compartment is separated from the anode compartment by an ion exchange membrane (e.g. Nafion ™ 425). The anode used is a platinum wire ring. An automatic potentiostat was used to control the potential between the cathode and the reference electrode. The anolyte used, unless specified otherwise, is a 1M solution of phosphate buffer with a pH of 2.7. The progress of the electrolyses were monitored with high performance liquid chromatography and thin layer chromatography. The reactions were run until such high performance liquid chromatography analysis and/or thin layer chromatographic analysis indicates that substantially all the standing material had been converted to product.

Also in the following examples, the abbreviations "HPLC", "n.m.r.", "i.r.", "v" and "f.d.m.s." stand for high performance liquid chromatography, nuclear magnetic resonance spectroscopy, infrared spectroscopy, volts and field desorption mass spectrometry, respectively. The abbreviations "e.a.", "THF", "NBS", "TMS" and "DMF" stand for elemental analysis, tetrahydrofuran, N-bromosuccinimide, tetramethylsilane and dimethylformamide, respectively. N.m.r. spectra used DMSO, assigned a δ value of 2.49, as the reference and were obtained on a 90 mHz instrument unless otherwise specified.

EXAMPLE 1

N-[Benzhydryl 3'-hydroxymethyl-2'-yl-2'-(R,S)-but-3'-enoate]-2-(R)-(sodium sulfinate)-3-(S)-[2-(thien-2-yl)-acetamido]-4-oxo-azetidine.

To a solution composed of methanol (34 ml) and acetic acid (2 ml) was added sufficient sodium perchlorate to give a 0.1 M concentration. Benzhydryl 7-(S)-[2-(thien-2-yl)acetamido]-3-hydroxymethyl-3-cephem-4-carboxylate sulfone (1.0 g) was added to the resultant solution. This solution was added to the cathode compartment of an electrolytic cell consisting of a mecury pool cathode and a platinum anode contained in cell compartments separated by a cation exchange membrane. The cell temperature was maintained at 0° C. during the following electrolysis. The cathode potential was adjusted to −1.4V and maintained at that potential until completion of the electrolysis. The progress of the electrolysis was monitored by HPLC analysis of the cathode solution and the electrolysis was stopped when analysis showed that substantially all of the cephem starting material had been converted to azetidine sulfinic acid salt product. At the end of the electrolysis the cathode solution was removed from the cathode compartment, a 1:1 0.3 M pH 7 phosphate: saturated sodium chloride solution was added to the solution, and the resultant mixture was extracted twice with ethyl acetate. The combined ethyl acetate extracts were washed twice with 100 ml portions of a 1:1 0.3 M pH 7 phosphate:saturated sodium chloride solution. The ethyl acetate extracts were dried over magnesium sulfate, filtered and the ethyl acetate was removed under reduced pressure. The resultant white foam residue was crude product, N-(benzhydryl 3'-hydroxymethyl-2'-yl-2'-(R,S)-but-3'-enoate)-2-(R)-(sodium sulfinate)-3-(S)-[2-(thien-2-yl)-acetamido]-4-oxo azetidine (568 mg). The crude product was purified by HPLC using a Water's Associates C₈ RCM column and 48% methanol in water with 1% sodium chloride as the eluent at a flow rate of 2.0 ml/min. The HPLC separated the desired product from the impurities and also separated the 2'-(R) and the 2'-(S) isomers of the product. The desired product was collected from the column, most of the methanol was removed under reduced pressure and the concentrate was extracted with ethyl acetate. The extracts were combined, dried over magnesium sulfate, filtered and the ethyl acetate was removed under reduced pressure. The n.m.r. of the resultant residue was as follows: n.m.r. (DMSO/d₆): 2'-(S)-isomer: 3.63 (d, 1, J=2.5, C-2 H), 3.66

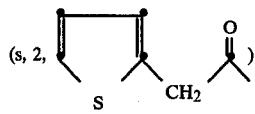

4.01

4.71 (dd, 1, C-3 proton $J^{NH}=8$, $J^{C-2H}=2.5$), 4.77

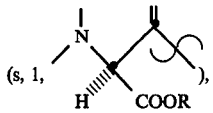

5.12, 5.36

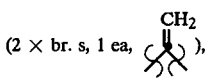

6.7 to 7.6 (m, 3, 4 and 5-thienyl and phenyl protons), 6.88 (s, 1, CO₂CH$\phi$₂), 8.76 (d, J=8, amido proton).
2'-(R)-isomer: 3.65

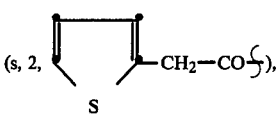

3.82 (d, 2, J=2.5, C-2 proton), 3.98

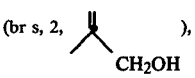

4.80 (dd, $J^{NH}=8$, $J^{C-2H}=2.5$, C-3 H), 4.95 and 5.19

(2 × br. s, 1 each, 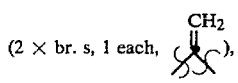), 5.11

(s, N—CH—COOR), 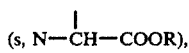

6.7 to 7.6 (m, 3, 4, 5 thienyl and phenyl protons), 6.80 (s, 1, CO₂CH̲φ₂), 8.71 (d, 1, J=8, amido proton).

EXAMPLE 2

N-(Benzhydryl 3'-hydroxymethyl-2'-yl-2'-(R,S)-but-3'-enoate)-2-(R)-(sodium sulfinate)-3-(S)-(2-phenoxyacetamido)-4-oxo-azetidine.

To a solution composed of methanol (34 ml) and acetic acid (2 ml) was added a sufficient amount of tetraethylammonium perchlorate to render the solution 0.1M in this inorganic salt. Benzhydryl 7-(S)-(2-phenoxyacetamido)-3-hydroxymethyl-3-cephem-4-carboxylate sulfone (1.0 g) was added to the resultant solution. This solution was added to the cathode compartment of the electrolytic cell. The anolyte had a pH of 3.6 and the cell temperature was maintained at 0° C. during the following electrolysis. The cathode potential was maintained at −1.375V and, when the HPLC analysis showed that the electrolysis was completed, the cathode solution was removed from the cathode compartment and a 1:1 saturated sodium chloride solution: 0.3M pH 7 phosphate buffer solution (100 ml) was added. This solution was then extracted twice with ethyl acetate, the ethyl acetate extracts were combined and washed three times with more of the above sodium chloride/buffer solution. The organic layer was then dried over anhydrous magnesium sulfate, filtered and the solvent was removed under reduced pressure to yield a white foam. The foam was dissolved in ethyl acetate, washed again with additional sodium chloride/buffer solution, and the organic layer was dried over magnesium sulfate, filtered and the solvent was removed under reduced pressure to yield the desired product, N-(benzhydryl 3'-hydroxymethyl-2'-yl-2'-(R,S)-but-3'-enoate)-2-(R)-(sodium sulfinate-3-(S)-(2-phenoxyacetamido)-4-oxo-azetidine (675 mg). Before characterizing the above product by n.m.r., the product was purified by HPLC. The HPLC separated the desired product from the impurities and also separated the 2'-(R) and the 2'-(S) isomers of the product. The parameters for the HPLC separation include an eluent of 52% methanol in water with a 1% concentration of sodium chloride, with a flow rate of 2.0 ml/min on a Water's Associates C₈ RCM column. n.m.r.: (DMSO/d₆) 2'-(R)-isomer: 3.85 (d, 1, J=2.5, C-2H), 4.00

(br.s., 2, ), 4.47

(s, 2, 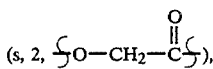), 4.84 (dd, 1, J=8, 2.5, C-3H), 4.99 and 5.20

(2 × br. s., 2, 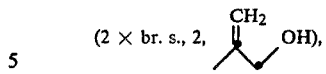), 5.13

(d, 1, N—CH—COOCH̲φ₂), 6.7 to 7.6 (m, 5, phenyl), 6.81 (s, 1, COOCH̲Ph₂), 8.70 (d, 1, J=8, NH̲); 2'-(S)-isomer: 3.76 (d, 1, J=2.5, C-2H), 4.03

(ABq, 2, ), 4.48

(s, 2, ), 4.77 and 5.12

(2 × br. s., 1 each, 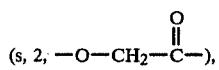), 4.78 (dd, 1, J=8, 2.5, C-3 H) 5.35

(s, 1, N—CH—CO₂CHPh₂), 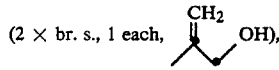

6.7 to 7.6 (m, 10, phenyls), 6.85 (s, 1, CO₂CH̲Ph₂), 8.68 (d, 1, J=8, NH̲).

EXAMPLE 3

N-(Benzhydryl 3'-hydroxymethyl-2'-yl-2'-(R,S)-but-3'-enoate)-2-(R)-(sodium sulfinate)-3-(S)-(2-phenylacetamido)-4-oxo-azetidine.

To a solution composed of methanol (34 ml) and acetic acid (2 ml) was added a sufficient amount of sodium perchlorate to render the solution 0.1M in this inorganic salt. Benzhydryl 7-(S)-(2-phenylacetamido)-3-hydroxymethyl-3-cephem-4-carboxylate sulfone (1.0 g) was added to the resultant solution. This solution was added to the cathode compartment of the electrolytic cell. The cell temperature was maintained at 0° C. during the following electrolysis. The cathode potential was maintained at −1.525V. When the electrolysis was completed, the cathode solution was removed from the cathode compartment and a 1:1 saturated sodium chloride solution: 0.3 M pH 7 phosphate buffer solution (100 ml) was added. This solution was then extracted twice with ethyl acetate, the ethyl acetate extracts were combined and washed (2X) with more of the above sodium chloride:buffer solution. The organic layer was dried over magnesium sulfate, filtered and the solvent was removed under reduced pressure to yield a white foam. The white foam was the desired product, N-(benzhydryl 3'-hydroxymethyl-2'-yl-2'-(R,S)-but-3'-enoate)-2-(R)-(sodium sulfinate)-3-(S)-(2-phenylacetamido)-4- oxo-azetidine. Before characterizing the above product by n.m.r., the product was purified with HPLC. The HPLC separated the desired product from the impurities and also separated the 2'-(R) and the 2'-(S) isomers of the product. The parameters for the HPLC separation include an eluent of 48% methanol in water with a 1% concentration of sodium chloride, a flow rate of 3.0 ml/min on a Water's Associates C8 RCM column. n.m.r.: (DMSO/d6) 2'-(R)-siomer: 3.43

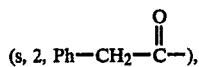

3.85 (d, 1, J=2.5, C-2H), 3.97

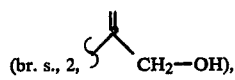

4.77 (dd, 1, J=2.5, 8, C-3H), 4.96 and 5.17

5.10

6.80 (s, 1, CO2C$\underline{H}$Ph2), 7.15 to 7.60 (m, 5, phenyl), 8.66 (d, 1, J=8, N$\underline{H}$); 2'-(S)-isomer: 3.4 (s, 2, PH-CH2CO—), 3.63 (d, 1, J=2.5, C-2H), 4.01

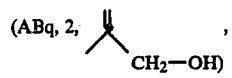

4.70 (dd, 1, J=2.5, 8.0, C-3H), 4.76 and 5.38

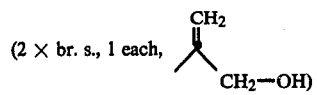

5.12

6.85 (s, 1, CO2C$\underline{H}$Ph2), 7.1 to 7.6 (m, 10, phenyl), 8.73 (d, 1, J=8, N$\underline{H}$).

EXAMPLE 4

N-[Benzhydryl 3'-hydroxymethyl-2'-yl-2'-(R,S)-but-3'-enoate]-2-(R)-sodium sulfinate)-3-(S)-[D-((5-(-2,4-dichlorobenzoxycarbonylamino))-5-(benzhydryl carboxylate)valeramido]-4-oxo-azetidine.

To a solution composed of methanol (34 ml) and acetic acid (2 ml) was added a sufficient amount of sodium perchlorate to render the solution 0.1M in this inorganic salt. Benzhydryl 7-(S)-[D-(5-(2,4-dichlorobenzoxycarbonylamino))-5-(benzhydryl carboxylate)valeramido]-3-hydroxymethyl-3-cephem-4-carboxylate sulfone (1.0 g) was added to the resultant solution. The solution was added to the cathode compartment of an electrolytic cell. The cell temperature was maintained at 0° C. during the following electrolysis. The cathode potential was maintained at −1.55V. When the electrolysis was completed, the catholyte was removed from the cathode compartment and a 1:1 saturated sodium chloride solution: 0.3M pH 7 phosphate buffer solution (100 ml) was added to the catholyte. This catholyte solution was then extracted twice with ethyl acetate, and the combined ethyl acetate extracts were washed an additional two times with the above sodium chloride:buffer solution. The organic layer was then dried over magnesium sulfate, filtered and the solvent was removed under reduced pressure to yield as a white foam the desired product, N-[benzhydryl 3'-hydroxymethyl-2'-yl-2'-(R,S)-but-3'-enoate]-2-(R)-(sodium sulfinate)-3-(S)-[D-(5-(2,4-dichlorobenzoxycarbonylamino))-5-(benzhydryl carboxylate)valeramido]-4-oxo-azetidine. Before characterizing the above product by n.m.r., the product was purified with HPLC. The parameters for this HPLC separation include an eluent of 62.5% methanol in water with a 1% concentration of sodium chloride, and a flow rate of 2.5 ml/min on a Water's Associates C8 RCM-100 column. This HPLC separated the desired product from the impurities and also separated the 2'-(R) and the 2'-(S) isomers of the product. n.m.r. (DMSO/d6) 2'-(R)-isomer: 0.7 to 2.3 (m, 6, methylene units in valeramido group), 3.82 (d, 1, J=2.5, C-2H), 3.99

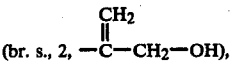

4.54 (m, 1, 5-carbon methine proton of valeramido group), 4.80 (dd, 1, J=2.5, 8, C-3H), 4.96 and 5.20

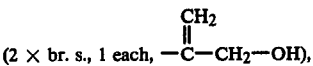

5.12

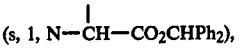

6.80 (s, 2, 2×CO2C$\underline{H}$Ph2), 7.2 to 7.7 (m, 23, 2×CO2CHP$\underline{h}$2, 2,4-dichlorophenyl), 8.43 (d, 1, J=8, 1-N$\underline{H}$), 8.99 (d, 1, J=8, amide-N$\underline{H}$); 2'-(S)-isomer: 0.8 to 2.3 (m, 6, methylene protons in valeramido group), 3.64 (d, 1, J=2.5, C-2H), 4.07

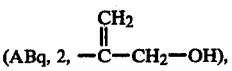

4.52 (m, 1, 5-carbon methine proton of valeramido group), 4.70 (dd, 1, J=2.5, 8, C-3H), 4.75 and 5.38

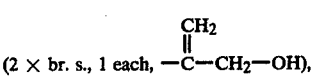

5.13

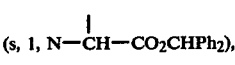

6.80 to 6.85 (singlets, 2, CO$_2$CHPh$_2$), 7.15 to 7.7 (m, 23, aromatic protons), 8.45 (d, 1, J=8 amide-NH), 8.99 (d, 1, J=8, 5-NH).

EXAMPLE 5

N-(Benzhydryl 3'-hydroxymethyl-2'-yl-2'-(R,S)-but-3'-enoate)-2-(R)-(sodium sulfinate)-3-(S)-p-toluylamido)-4-oxo-azetidine.

To a solution composed of methanol (34 ml) and acetic acid (2 ml) was added sufficient lithium chloride to give a 0.5 M concentration. Benzhydryl 7-(S)-(p-toluylamido)-3-hydroxymethyl-3-cephem-4-carboxylate sulfone (2.0 g) was added to the solution. The sulfone-containing solution was added to the cathode compartment of the electrolytic cell. The cell temperature was maintained at 0° C. during the electrolysis. The cathode potential was −1.38V. When the electrolysis was complete the cathode solution was removed from the cathode compartment and was extracted with ethyl acetate. The extract was washed with a 1:1 0.3 M pH 7 phosphate:saturated sodium chloride solution, dried over magnesium sulfate, filtered and evaporated under reduced pressure. Approximately 3.5 mg of the crude product mixture was purified by HPLC, using a Water's Associates C$_{18}$ preparatory column and 52% methanol in water with 1% sodium chloride at a flow rate of 3.0 ml/min. The HPLC separated the desired product from the impurities and also separated the 2'-(R) and the 2'-(S) isomers of the product. The methanol from the separate fractions containing the 2'-(R) and 2'-(S) isomers was removed under reduced pressure and each fraction was lyophilized. Each fraction was dissolved in methylene chloride and the remaining sodium chloride was removed by filtration. The methylene chloride solutions were each then dried over magnesium sulfate, filtered, and taken to dryness.

The above procedure was repeated three more times on solutions containing about 3 mg of the crude reaction mixture. The fractions containing the 2'-(R) and 2'-(S) were combined separately. The following spectral data was obtained for the purified products, N-(benzhydryl 3'-hydroxymethyl-2'-yl-(2'-(R) or 2'-(S))-but-3'-enoate)-2-(R)-(sodium sulfinate)-3-(S)-(p-toluylamido)-4-oxo-azetidine: n.m.r. (DMSOd$_6$, reference was TMS) (2'-(R)-isomer): δ 2.34 (s, 3, para-methyl group), 3.91 (d, 1, C$_2$-H), 4.03 (s, 2, CH$_2$ of C$_3$' hydroxymethyl) 4.90 (dd, 1, C$_3$-H, J$^{NH}$=8, J$^{C_2-H}$=2.5), 5.02 (s, 1, C$_4$'-H), 5.16 (s, 1, C$_2$'-H), 5.21 (s, 1, C$_4$'-H), 6.79 (s, 1, methine proton of benzhydryl ester), 7.05-7.8 (m, 14, aromatic protons), 8.92 (d, 1, amido proton, J$^{C_3H}$=8). 2'-(S)-isomer: δ 2.34 (s, 3, paramethyl protons), 3.88 (d, 1, C$_2$-H, J$^{C_3H}$=2.5), 4.26 (ABq, 2, methylene group of C$_3$' hydroxymethyl), 4.80 (s, 1, C$_4$'-H), 4.89 (dd, 1, C$_2$-H, J$^{C_3H}$=2.5, J$^{NH}$=8), 5.14 (s, 1, C$_4$'-H), 5.34 (s, 1, C$_2$'-H), 6.89 (s, 1, methine proton of benzhydryl ester), 7.1 to 7.8 (m, 14, aromatic protons), 8.90 (d, 1, amido proton, J$^{C_3H}$=8).

EXAMPLE 6

N-(Sodium 3'-hydroxymethyl-2'-yl-2'-(R,S)-but-3'-enoate)-2-(R)-(sodium sulfinate)-3-(S)-(2-phenoxyacetamido)-4-oxo-azetidine.

Sodium 7-(S)(2-phenoxyacetamido)-3-hydroxymethyl-3-cephem-4-carboxylate sulfone (1.0 g) was dissolved in a 0.25M aqueous sodium sulfate solution (35 ml). The resultant solution was added to the cathode compartment of an electrolytic cell containing a mercury pool cathode having a surface area of 14 cm$^2$ and in which the cell compartments were separated by a microporous frit. The anolyte solution's pH was controlled at approximately 5 (range: 4.5–5.1) by the addition of 0.1N sulfuric acid. The cell temperature was maintained at 10° C. throughout the electrolysis. The cathode potential was adjusted to −1.85V and maintained at that potential throughout the electrolysis. When the electrolysis was completed the catholyte was transferred to another flask and lyophilized overnight. The n.m.r. of the lyophilized product N-(sodium 3'-hydroxymethyl-2'-yl-2'-(R,S)-but-3'-enoate)-2-(R)-(sodium sulfinate -3-(S)-(2-phenoxyacetamido)-4-oxo-azetidine, is as follows: n.m.r. (DMSO/d$_6$): 2'-(R) isomer: δ 3.84, (d, 1, J=2.9, C-2H), 3.98

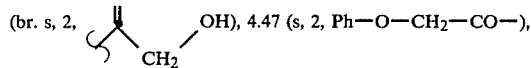

(br. s, 2, OH), 4.47 (s, 2, Ph—O—CH$_2$—CO—), 4.47 (s, 1, one of the C-4' protons), 4.86, 4.95 (dd, J$^{C-2H}$=2.9, J$^{NH}$=8, C-3 H), 5.09 (br. s, 1, one of the C-4' protons), 5.09 (br. s, 1, C-2'H), 6.84 to 7.30 (m, 5, phenyl protons), 8.82 (d, 1, amido proton).

EXAMPLE 7

N-(3'-Hydroxymethyl-2'-yl-2'-(R,S)-but-3'-enoic acid)-2-(R)-(sulfinic acid)-3-(S)-(p-toluylamido)-4-oxoazetidine.

Sodium 7-(S)-(p-toluylamido)-3-hydroxymethyl-3-cephem-4-carboxylate sulfone (1 g) was dissolved in 0.25 M aqueous sodium sulfate solution (35 ml). The resultant solution was added to the cathode compartment of an electrolytic cell, containing a mercury pool cathode having a surface area of 14 cm$^2$ and in which the cell compartments were separated by microporous frit. The pH of the anolyte solution was controlled at 7 by the addition of 1 N sulfuric acid. The cell temperature was maintained at 10° C. throughout the electrolysis. The cathode potential was adjusted to −1.85V and maintained at that potential throughout the electrolysis. Following the electrolysis the catholyte was then transferred to another flask. Ethyl acetate (40 ml) was added and the mixture was chilled. Sulfuric acid (12 N) was added to the mixture until the aqueous layer had a pH of 1.5. The ethyl acetate layer was then separated and combined with the ethyl acetate layer from the second extraction of the catholyte, under identical conditions. The ethyl acetate was evaporated to yield 300 mg of residue, and the residue was taken up in the minimum amount of ethyl acetate and crystallized in the refrigerator to yield 46 mg of residue. This crystallized product yielded N-(3'-hydroxymethyl-2'-yl-2'-(S)-but-3' -enoic acid)-2-(R)-(sulfinic acid)- 3-(S)-(p-toluylamido)-4-oxoazetidine. n.m.r: (DMSO/d$_6$, reference was TMS) δ 2.34 (s, 3, para-methyl protons), 4.13

(s, 2, OH), 4.57 (d, 1, J=2.9, C-2'H), 4.88 (s, 1, C-2'H), 5.08 (dd, 2, J$^{NH}$=8, J$^{C-2H}$=2.9, C-3H (2nd doublet under peak at δ5.18), 5.18

(br. s, 2, one of doublets from dd at 5.08, and one of two 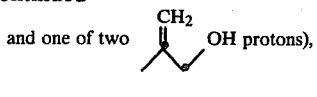 OH protons), 5.43

(br. s, 1, one of two 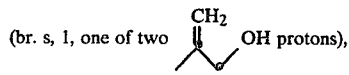 OH protons), 7.1 to 7.9 (m, 4, aromatic protons), 9.22 (d, 1, J=8, amido proton).

EXAMPLE 8

Benzhydryl (2'-(R,S))-2'-[(1R,5S)-3-[D-(4-(2,4-dichlorobenzoxycarbonylamino))-4-(benzhydryl carboxylate)-but-1-yl]-7-oxo-4-oxa-2,6-diazabicyclo-[3.2.0]hept-2-en-6-yl]-4'-hydroxy-3'-exomethylene butyrate.

Procedure A a. Electrolysis A solution of methanol (48.0 ml) and acetic acid (3.0 ml) was mad 0.1 M in sodium acetate and then benzhydryl 7-(S)-[D-(5-(2,4-dichlorobenzoxycarbonylamino))-5-(benzhydryl carboxylate)-valeramido]-3-hydroxymethyl-3-cephem-4-carboxylate sulfone (4.0 g) was added. The solution was then added to the cathode compartment of an electrolytic cell, thermostated at 0° C., containing a lead plate cathode and a platinum anode separated by a cation exchange membrane. The electrolysis was conducted at a constant current of 400 ma (19 ma/cm$^2$) until HPLC analysis of the catholyte showed the electrolysis to be complete.

b. NBS Oxidation The catholyte was transferred to a flask and chilled to approximately 0° C. in an alcohol/ice bath. A methanol solution (50 ml) of N-bromosuccinimide (1.18 g) was slowly added to the cold catholyte with constant stirring. At the end of the addition HPLC of the resultant solution showed the oxidation to be complete. To this solution containing the oxazoline azetidinone product was added an aqueous solution of 1:1 0.3 M phosphate solution at pH 7: saturated sodium chloride solution containing 1% sodium hydrogen sulfite. This buffered solution was then extracted twice with ethyl acetate, the two ethyl acetate layers were combined and washed again with the above 1:1 0.3 M phosphate solution/saturated sodium chloride solution, dried over magnesium sulfate, filtered, and the solvent removed in vacuo to yield foam. A preparative thin layer chromatogram (using a 3:2 v:v ethyl acetate:toluene eluant) of a small amount of this foam yielded benzhydryl (2'-(R)-2'-((1R,5S)-3-[D-(4-(2,4-dichlorobenzyloxycarbonylamino))-4-(benzhydryl carboxylate)-but-1-yl]-7-oxo-4-oxa-2,6-diazabicyclo[3.2.0-]hept-2-en-6yl)-4'-hydroxy-3'-exomethylene butyrate and the corresponding 2'-(S)-isomer. n.m.r: (CDCl$_3$, reference was TMS) C-2'-(S)-isomer; δ 0.8 to 2.6 (m, 6, (—CH$_2$—)$_3$), 4.04

(ab quartet, 2, 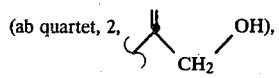 OH), 4.96 (m, 1, 4-methine proton of butyl group), 4.96 (s, 1, C-2'H), 5.03, 5.28 (2×(s, 1, exomethylene proton)), 5.06 (d, 1, C-1H), 6.10 (d, 2, C-5H), 6.89, 6.92 (2×(s, 1, benzhydryl group methine protons)), 7 to 7.8 (m, 24, aromatic protons and amido proton); b 2'-(R)-isomer (CDCl-3, reference was TMS): δ 0.8 to 2.6 (m, 6, (—CH$_2$—)$_3$), 4.2

(ab quartet, 2,  OH), 4.9 (m, 1, 4-methine proton of butyl group), 4.95 (s, 1, C-2'H, 5.01 (d, 1, C-1 H), 5.1, 5.37 (2×(s, 1, exomethylene proton)), 5.75 (d, 1, C-5 H), 6.87, 6.91 (2×(s, 1, benzhydryl group methine proton)), 7 to 7.8 (m, 24, aromatic and amido group protons).

Procedure B a. Electrolysis A solution of acetonitrile (25.5 ml), water (8.5 ml) and acetic acid (2 ml) was made 0.1 M in tetraethylammonium perchlorate. Benzhydryl 7-(S)-[D-(5-(2,4-dichlorobenzoxycarbonylamino))-5-(benzhydryl carboxylate)valeramido]-3-hydroxymethyl-3-cephem-4-carboxylate sulfone (1 g) was added to this solution. This solution was in turn added to this solution. This solution was in turn added to the cathode compartment of an electrolytic cell thermostatted at 0° C. The anolyte, a 1.0 M tetraethylammonium acetate buffer (pH 3.6), was added to the anode compartment, and the catholyte was deoxygenated by a stream of argon. The electrolysis was carried out by applying a potential of −1.50V to the cathode, and maintaining this potential until the current had diminished to zero and HPLC analysis of the cathode solution demonstrated that the starting material had all been consumed.

b. Lead tetraacetate oxidation The catholyte solution was then removed from the cathode compartment and chilled ethyl acetate (90 ml) was added. The layers were separated and the ethyl acetate layer was washed with chilled 0.3 M phosphate buffer (40 ml, 3X) and with saturated sodium chloride solution (40 ml, 1X). The ethyl acetate solution was dried over sodium sulfate, filtered and a small volume (8 m) was removed for n.m.r. analysis. The volume of the remaining solution was reduced to approximately 25 ml. This solution was chilled and lead tetraacetate (1 mM) was added while stirring, followed by the addition of another portion (88 mg) of lead tetraacetate. When HPLC analysis of the reaction mixture indicated the reaction to be complete, the precipitate was removed by vacuum filtration and the ethyl acetate filtrate was washed with 1:1 saturated sodium chloride: 0.3 M pH 7 phosphate buffer solution (25 ml, 2X), dried over sodium sulfate, filtered and evaporated to dryness under vacuum to yield 557 mg of foam. A small portion of this material (40 mg) was subjected to HPLC on a Water's Associates C$_{18}$ preparatory column using 30% water in acetonitrile as the eluant. Benzhydryl (2'-(S))-2'-[(1R,5S)-3-[D-(4-(2,4-dichlorobenzyloxycarbonylamino))-4-(benzhydryl carboxylate)-but-1-yl]-7-oxo-4-oxa-2,6-diazabicyclo[3.2.0-]hept-2-en-6:yl]-4'-hydroxy-3'-exomethylenebutyrate (14 mg) was recovered. The n.m.r. (CDCl$_3$, reference was TMS) of this compound showed a doublet at δ 6.1 with a coupling constant of 3.2 Hz, indicating that the compound was the 2'-(S)-isomer.

EXAMPLE 9

Benzhydryl (2'-(R,S))-2'-[(1R,5S)-3-(p-toluyl)-7-oxo-4-oxa-2,6-diazabicyclo[3.2.0]hept-2-en-6-yl]-4'-hydroxy-3'-exomethylene butyrate.

Procedure A

A. Electrolysis A solution of methanol (34 ml) and acetic acid (2.0 ml) was made 0.5 M in sodium perchlorate. Benzhydryl 7-(S)-(p-toluylamido)-3-hydroxymethyl-3-cephem-4-carboxylate (4.0 g) was added to this solution and the resultant mixture was added to the cathode compartment of an electrolytic cell thermostatted at 0° C. The catholyte was deoxygenated with a small stream of argon. The electrolysis was begun at a cathodic current of 750 ma (37.5 ma/cm$^2$) and gradually stepped down to 50 ma over a 3000 second time period. At the end of this time period, HPLC analysis of the catholyte indicated that the reduction was very near completion and the electrolysis was stopped.

B. NBS Oxidation The catholyte was then transferred to a flask and chilled to 0° C. in an alcohol-ice bath. A methanol solution (50 ml) of N:bromosuccinimide (1.96 g) was then added to the chilled catholyte over a ten minute period, at the end of which time period HPLC analysis of the resultant reaction mixture indicated that the oxidation was complete. A 1:1 0.3 M pH 7 phosphate:saturated sodium chloride solution that was 1% in sodium hydrogen sulfite was added to the reaction mixture, and the resultant solution was extracted twice with ethyl acetate. The ethyl acetate layers were combined, washed three times with the above 1% sodium hydrogen sulfite solution, dried over magnesium sulfate, filtered and evaporated to dryness in vacuo, to yield a white foam. This white foam contained crude benzhydryl (2'-(R,S))-2'-[(1R,5S)-3-(p-toluyl)-7-oxo-4-oxa-2,6-diazobicyclo[3.2.0]hept-2-en-6-yl]-4'-hydroxy-3'-exomethylene butyrate (3.32 g, 94% crude yield). This crude product mixture was recrystallized from 1:3 hexanes/toluene (15 ml) to yield 2.03 g of a mixture of the 2'-(R) and 2'-(S) isomers. N.M.R. analysis of the crude product mixture showed that the 2'-(R) and 2'-(S) isomers were present in approximately equal amounts and that 5 to 10% of the crude product mixture was the lactone of the following structure:

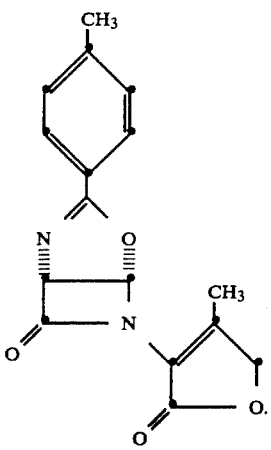

The amounts of each compound present were determined by the ratio of the areas under the peaks for the C-5 proton of each molecule. Similarly, n.m.r. analysis of the recrystallized product mixture shows that only the 2'-(R) and 2'-(S) isomers (no lactone) are present in equal amounts. The n.m.r. of the crude product mixture and recrystallized product mixture showed the chemical shifts of the characteristic C-5 protons of the above molecules to be as follows: n.m.r. (DMSOd$_6$, reference was TMS): 2'-(R)-isomer, δ 6.10; 2'-(S) isomer (reference was DMSO), δ 6.28; lactone, δ 6.65.

Procedure B

A. Electrolysis A solution of methanol (48 ml) and acetic acid (3.0 ml) was made 0.5 M in sodium perchlorate. Benzhydryl 7-(S)-(p-toluylamido)-3-hydroxymethyl-3-cephem-4-carboxylate (3.0 g) was added to this solution and the resultant mixture was added to the cathode compartment of an electrolytic cell containing a zinc cathode (24 cm$^2$) and thermostatted at 0° C. The electrolysis was conducted at a cathodic current of 21 ma/cm$^2$.

B. NBS Oxidation When the above electrolysis was completed, the catholyte was transferred to a flask and chilled to 0° C. in an alcohol/ice bath. A methanol solution (50 ml) of N-bromosuccinimide (1.47 g) was added to the chilled catholyte slowly through a dropping funnel, and at the end of the addition HPLC analysis of the resultant reaction mixture indicated that the oxidation was complete. A 1:1 0.3 M pH 7 phosphate:saturated chloride solution that was 1% in sodium hydrogen sulfite was added to the reaction mixture, and the resultant solution was extracted twice with ethyl acetate. The ethyl acetate layers were combined, washed three times with a 1:1 0.3 M pH 7 phosphate:saturated sodium chloride solution, dried over magnesium sulfate, filtered, concentrated and placed in a refrigerator. The chilled concentrate was filtered to yield 1.477 g of crystals of the title product. n.m.r. (major identifying peaks only) (DMSOd$_6$,reference was TMS): δ6.18 (d, 1, C-5 proton of 2'-(R)-isomer), 6.38 (d, 1, C-5 proton of 2'-(S)-isomer).

Procedure C

A. Electrolysis A solution of methanol (48 ml) and acetic acid (4 ml) was made 0.1 M in sodium acetate. Behzhydryl 7-(S)-(p-toluylamido)-3-hydroxymethyl-3-cephem-4-carboxylate (4.0 g) to this solution and the resultant mixture was added to the cathode compartment of an electrolyte cell containing a lead plate cathode (24 cm$^2$) and thermostatted at 0° C. The electrolysis was conducted at 25 ma/cm$^2$ for approximately 3500 seconds.

B. NBS Oxidation When the electrolysis was completed, the catholyte was transferred to a flask and chilled to 0° C. in an ice/alcohol bath. A methanol solution (approximately 50 ml) of N-bromosuccinimide (1.5 equivalents) was added to the chilled catholyte slowly through a dropping funnel. When the HPLC analysis of the solution indicated that the oxidation reaction was complete, a 1:1 0.3 M pH 7 phosphate:saturated sodium chloride solution that was 1% in sodium hydrogen sulfite was added to the reaction mixture, and the resultant solution was extracted with ethyl acetate (2X). The ethyl acetate layers were combined, washed with 1:1 0.3 M pH 7 phosphate:saturated sodium chloride solution (3X), dried over magnesium sulfate, filtered, concentrated and placed in the refrigerator. The chilled solution was filtered to collect crystals (2.57 g) of the title product, n.m.r. (major identifying peaks only) (DMSOd$_6$, reference was TMS): δ6.18 (d, 1, C-5 proton of 2′-(R)-isomer), 6.38 (d, 1, C-5 proton of 2′-(S)-isomer).

EXAMPLE 10

Benzhydryl (2′-(R,S))-2′-[(1R,5S)-3-(2-(thien-2-yl)methyl)-7-oxo-4-oxa-2,6-diazabicyclo[3.2.0]hept-2-en-6-yl]-4′-hydroxy-3′-exomethylene butyrate.

A. Electrolysis A solution of 10% water in DMF (35 ml) and acetic acid (2.0 ml) was made 0.1 N in tetraethylammonium perchlorate. Benzhydryl 7-(S)-[2-(thien-2-yl)acetamido]-3-hydroxymethyl-3-cephem-4-carboxylate (2.0 g) was added to this solution and the resultant mixture was added to the cathode compartment of an electrolytic cell thermostated at 0° C. An anode compartment containing a cation exchange membrane separator and a platinum anode in a pH 3.6 1 N acetate buffer was then placed in the cathode compartment of the electrolytic cell. The catholyte was de-oxygenated with a small stream of argon. The electrolysis was done by adjusting the cathodic current to 150 ma (10.7 ma/cm$^2$) and maintaining that current throughout the electrolysis.

B. Lead Tetraacetate Oxidation The catholyte was removed from the cathode and acidic sodium chloride solution was added. The solution was extracted with ethyl acetate and the extract was washed with portions of acidic sodium chloride solution, then dried over anhydrous magnesium sulfate and filtered. The filtrate was chilled to 0° C. in an alcohol/ice bath. Lead tetraacetate (1.6 g) was added to the ethyl acetate solution and allowed to react for 15 minutes at 0° C. At the end of this time the lead tetraacetate was removed by filtration and the ethyl acetate filtrate was washed several times with a pH 7.0 0.3 N phosphate solution. The ethyl acetate filtrate was then dried over magnesium sulfate, filtered and evaporated under reduced pressure to yield a light yellow foam. This foam contained predominantly the C-2′-(S)-isomer of benzhydryl (2′-(R,S))-2′-[(1R,5S)-3-(2-(thien-2-yl)-methyl)-7-oxo-4-oxa-2,6-diazabicyclo[3.2.0]hept-2-en-6-yl]-4′-hydroxyl-3′-exomethylene butyrate. n.m.r.: (DMSOd$_6$): (major identifying peak only) δ 6.10 (d, 1, C-5H).

EXAMPLE 11

Sodium (2′-(R,S))-2′-[(1R,5S)-3-(p-toluyl)-7-oxo-4-oxa-2,6-diazabicyclo[3.2.0]hept-2-en-6-yl]-4′-hydroxy-3′-exomethylene butyrate.

Procedure A a. Electrolysis Sodium 7-(S)-(p-toluylamido)-3-hydroxymethyl-3-cephem-4-carboxylate (1.0 g) was dissolved in an aqueous 0.25 M sodium sulfate solution. The solution was added to the cathode compartment of an electrolytic cell wherein the cell compartments were separated by a Nafion ™ 427 cation exchange membrane. The anolyte was also an Aqueous 0.25 M sodium sulfate solution. The pH of the catholyte was set at 5.5 and maintained at that value during the electrolysis by the addition of 0.1 N sulfuric acid. The cell was thermostatted at 10° C. and the potential of the cathode was maintained at −1.85V.

b. Oxidation The catholyte was removed from the cathode compartment, and 1 M phosphate solution (pH 7, 5 ml) and ethyl acetate (50 ml) were added to the catholyte. This solution was chilled in an ice-alcohol bath, then the pH of the solution was adjusted to 2.5 by the addition of 12 N sulfuric acid. A dimethylformamide solution (2 ml) of N-bromosuccinimide (800 mg) was added dropwise to the chilled solution over approximately 5 minutes, allowing the yellow color to dissipate after each addition. During this time the pH of the cooled reaction mixture changed from 2.5 to 1.8. Sodium bisulfite (200 mg) was added and the layers were allowed to separate. The aqueous layer was extracted with ethyl acetate (50 ml), all the while maintaining the two layers at low temperature by the addition of ice. The ethyl acetate layer and extract were combined then washed with a 0.1 N hydrochloric acid:saturated sodium chloride solution (50 ml, 2X). The ethyl acetate solution was then dried over magnesium sulfate and filtered. The filtrate was evaporated to the point of crystallization and then further evaporated until approximately 10 ml of filtrate remained. This solution was refrigerated overnight, yielding 406 mg (52%) of a 1:4 C-2′-(R):C-2′-(S) mixture of sodium (2′-(R,S))-2′-[(1R,5S)-3-(p-toluyl)-7-oxo-4-oxa-2,6-diazabicyclo[3.2.0]hept-2-en-6-yl]-4′-hydroxy-3′-exomethylene butyrate. n.m.r.: (DMSOd$_6$) C-2′-(S)-isomer: 2.32 (s, 3, para-methyl) 3.92

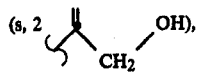

4.86 (s, 1, C-2′ H), 5.14, 5.34 (2 x (br. s., 1, exomethylene protons)), 5.40 (d, 1, C-1 H), 6.28 (d, 1, C-5 H), 7.22–7.88 (m, 4, aromatic protons); C-2′-(R)-isomer, the same as the C-2′-(S)-isomer except C-5 H absorbs at δ 6.05 instead of δ 6.28; f.d.m.s.: 316.

Procedure B a. Electrolysis The electrolysis was run as above, with the following changes: the anolyte and catholyte were both a 0.5 M aqueous sodium chloride solution. The cell compartments were separated by a microporous glass frit and the potential of the cathode was maintained at −1.85V throughout the electrolysis. Finally, the pH of the catholyte was set at 7 and maintained between 4.5 to 7.5 by the addition of 0.1 N hydrochloric acid.

b. Oxidation The catholyte was transferred from the cathode compartment and chilled in an ice-alcohol bath. To the chilled solution was added sodium bicarbonate (1.5 g) then a dimethylformamide solution (2 ml) of N-bromosuccinimide (399 mg). (The initial pH of the reaction mixture was 8.1, and the final pH was 7.4 and the minimum pH was 7.0). The progress of the reaction was monitored by HPLC. Approximately 0.5 hour after the first addition, a second addition of dimethylformamide solution (2 ml) of N-bromosuccinimide (289 mg) was made. Approximately 10 minutes later a third addition of N-bromosuccinimide (90 mg), dissolved in dimethylformamide, was made. Based on the HPLC analysis of the reaction mixture, 385 mg of a combination of the 2′-(R) and 2′-(S)-isomers was present.

Procedure C a. Electrolysis The electrolysis was run as in Procedure B, with the following changes: The catholyte and the anolyte were an aqueous 0.25 M sodium sulfate solution. The potential of the cathode was maintained at −1.85V throughout the electrolysis. The pH of the catholyte was maintained at 8.0 during the electrolysis by the addition of 0.1 N sulfuric acid. The pH of the catholyte ranged from 5 to 8.5 during the electrolysis.

b. Oxidation The catholyte was removed from the cathode compartment and layered with ethyl acetate (50 ml). The resulting mixture was chilled in an ice-alcohol bath, then NBS (469 mg) was added. The pH of the reaction mixture was 6.0, and the final pH was 2.0. The layers were allowed to separate and the ethyl acetate layer was washed with chilled 0.1 N hydrochloric acid-saturated sodium chloride solution (40 ml, 2X). The product was extracted into water by washing the ethyl acetate layer with 1:1 5% sodium bicarbonate:-saturated sodium chloride solution (40 ml, then 20 ml). The aqueous extracts were combined and stored in a freezer for approximately 0.75 h. The combined aqueous extracts were then placed in an ice-alcohol bath, then ethyl acetate (30 ml) was added. The pH of the aqueous layer was adjusted to 2.5 by the addition of 12 N sulfuric acid followed by the addition of 1 N sulfuric acid. The acidified aqueous layer was further extracted with ethyl acetate (30 ml, 2X), the three ethyl acetate extracts were combined, dried over magnesium sulfate and filtered. The filtrate was evaporated to the point of crystallization under reduced pressure and was placed in the refrigerator overnight. The crystallized product (160 mg) was collected by filtration. The n.m.r. spectrum of the product crystals (DMSOd$_6$) showed the product to be approximately an 85:15 mixture of 2'-(S) to 2'-(R)-isomer.

EXAMPLE 12

Benzhydryl (2'-(R,S))-2'-[(1R,5S)-3-(p-toluyl)-7-oxa-4-oxa-2,6-diazobicyclo[3.2.0]hept-2-en-6-yl]-4'-hydroxy-3'-exomethylene butyrate.

Procedure A a. Electrolysis Sodium 7-(S)-(p-toluylamido)-3-hydroxymethyl-3-cephem-4-carboxylate (1 g) was dissolved in an aqueous 0.25 M sodium sulfate solution (35 ml of water made 0.25 M in sodium sulfate). The solution was added to the cathode compartment of an electrolytic cell wherein the cell compartments were separated by a microporous frit. The anolyte was also an aqueous 0.25 M sodium sulfate solution. The initial pH of the catholyte solution was 7.0, with range being 6.0 to 8.5 during the electrolysis, controlled by the addition of 0.1 N sulfuric acid. The cell was thermostatted at 10° C. and the potential of the cathode was maintained at −1.86V.

b. Oxidation The catholyte was removed from the cathode compartment and chilled in an ice-alcohol bath. A DMF solution (2 ml) of NBS (422 mg) was added while the pH of the reaction mixture was controlled between 5 and 6 by the addition of 1 N sodium hydroxide solution. The reaction mixture was then layered with ethyl acetate (15 ml), diphenyldiazomethane (439 mg) was added, and the pH of the resultant reaction mixture was lowered to 2.5 by the addition of 1 N sulfuric acid. The reaction mixture was removed from the ice-alcohol bath and the pH of the mixture was maintained at 2.5 by the addition of 1 N sulfuric acid. After 1.5 h, the layers were separated, ethyl acetate (15 ml) was added to the ethyl acetate layer, and the ethyl acetate layer was washed with ice-chilled 0.1 N hydrochloric acid (40 ml, 3X) then with 1:1 0.3 M (pH 7) phosphate solution:saturated sodium chloride solution (3X, 40 ml). The ethyl acetate layer was dried over magnesium sulfate, filtered and stored in the refrigerator overnight. The solvent was removed under reduced pressure to yield 700 mg (58% of approximately 60%:40% C-2'-(S):C-2'-(R) benzhydryl (2'-(R,S))-2'-[(1R,5S)-3-(p-toluyl)-7-oxo-4-oxa-2,6-diazobicyclo[3.2.0]hept-2-en-6-yl]-4'-hydroxy-3'-exomethylene butyrate.

Procedure B a. Electrolysis The same basic procedure was used as in Procedure A, except for the following changes: the solvent used was 32.6 ml: 3.6 ml methanol:water solution, the catholyte is the solvent made 0.5 M in sodium perchlorate and 1 M in benzoic acid. Benzhydryl 7-(S)-(p-toluylamido)-3-hydroxymethyl-3-cephem-4-carboxylate (2 g) was the starting material, the cell compartments were separated by a Nafion™ 425 cation exchange membrane, the mercury pool cathode had an area of 20 cm$^2$, and the anolyte was a pH 2.7 phosphate solution (2% sodium dihydrogen phosphate). The cathode potential was maintained at −1.450V during the electrolysis and the cell was thermostatted at 0° C.

b. Oxidation The catholyte was removed from the cathode compartment, chilled in an ice-alcohol bath and recrystallized NBS (625 mg) was added. When HPLC analysis of the reaction mixture showed the reaction to be complete, a 1:1 0.3 M phosphate (pH 7) saturated sodium chloride/1% sodium bisulfite solution (50 ml) was added, which was followed by formation of a precipitate. Ethyl acetate (120 ml) was added to the reaction mixture, the layers were separated, and the aqueous layer was extracted with ethyl acetate (100 ml). The ethyl acetate layer and extract were combined, washed sequentially with a 1:1 0.3 M phosphate (pH 7) solution:saturated sodium chloride/1% sodium bisulfite solution (50 ml), chilled 0.1 N hydrochloric acid in saturated sodium chloride (3X, 50 ml), 5% sodium bicarbonate solution (80 ml, 3X) and finally with saturated sodium chloride (50 ml, 1X). The ethyl acetate layer was dried over magnesium sulfate, filtered and evaporated under reduced pressure to a foam. The foam was taken up in ethyl acetate and then washed with 5% sodium bicarbonate solution (50 ml, 3X). The ethyl acetate solution was dried over magnesium sulfate, filtered and evaporated under reduced pressure to give 1.1 g of foam. The foam was taken up in ethyl acetate (10 ml) and toluene (15 ml) was added. The ethyl acetate was evaporated under vacuum and the remaining solution was seeded with the oxazoline. The solution was refrigerated for two days and the resultant crystals were collected by filtration and washed with cold toluene. The crystals were dried under vacuum at room temperature to give 540 mg of a 40:60 2'-(S):2'-(R) mixture of isomers based on the integration for the respective C-5 protons in the n.m.r. The mother liquor from this crystallization was reduced to a volume of about 5 ml of toluene, seeded with 2'-(S) epioxazoline isomer and refrigerated for four days. The crystals (100 mg) were collected by filtration and contained a 1:1 mixture of C-2'-(R):C-2'-(S)-isomers.

Procedure C a. Electrolysis The electrolysis was carried out as in Procedure B, except that the solvent used was a solution of acetonitrile (32.4 ml)/water (3.6 ml) and the anolyte was 1 M (pH 3.6) sodium acetate.

b. Oxidation The catholyte was removed from the cathode, chilled in an ice-alcohol bath and recrystallized NBS (717.2 mg total) was added in two portions. When HPLC analysis of the reaction mixture showed the reaction to be complete, 1:1 (pH 7) 0.3 M phosphate:saturated sodium chloride/1% in sodium bisulfite (50 ml) was added. Ethyl acetate (80 ml) was added, the layers were separated and the ethyl acetate layer was washed sequentially with 1:1 0.3 M (pH 7) phosphate:saturated sodium chloride/1% sodium bisulfite solution (50 ml, 1X), 0.1 N hydrochloric acid saturated with sodium chloride (2X) then with 5% sodium bicarbonate (50 ml, 6X). The ethyl acetate layer was dried over magnesium sulfate, filtered and evaporated under reduced pressure to give 1 g of foam. HPLC analysis of this foam showed it to be a 1:1 mixture of C-2'-(R):C-2'-(S)-isomers.

Procedure D a. Electrolysis The electrolysis was carried out as in Procedure C, except that the solvent used was acetonitrile (30.4 ml)/water (3.6 ml)/acetic acid (2 ml), the potential of the cathode was −1.48V, and the catholyte was the solvent made 0.5 M in sodium perchlorate.

b. Oxidation The catholyte was removed from the cathode compartment, chilled in an ice-alcohol bath and NBS (652 mg; recrystallized from water) was added followed by a second addition of recrystallized NBS (81 mg). When HPLC analysis showed the reaction to be complete, 1:1 0.3 M (pH 7) phosphate:saturated sodium chloride/1% in sodium bisulfite (50 ml) was added. Ethyl acetate (80 ml) was added, the layers were separated, and the ethyl acetate layer was washed sequentially with 0.1 N hydrochloric acid saturated with sodium chloride (50 ml, 2X) and 1:1 0.3 M (pH 7) phosphate:saturated sodium chloride/1% in sodium bisulfite (50 ml, 1X). The ethyl acetate layer was dried over magnesium sulfate, filtered and the filtrate evaporated to yield a foam. The foam was dissolved in ethyl acetate (80 ml) and this solution was washed with 1:1 0.3 M (pH 7) phosphate:saturated sodium chloride/1% in sodium bisulfite (50 ml, 2X). The solution was again dried over magnesium sulfate, filtered and the filtrate evaporated to give 1.1 g of foam. The foam was dissolved in a 1:1 ethyl acetate:toluene solvent (10 ml) and the volume of this solution was reduced to about 5 ml. The solution was seeded with crystals of the 2'-(S) epioxazoline isomer, then refrigerated for 2.5 days. The crystals (222 mg) were collected by filtration and washed with cold toluene. n.m.r. analysis showed these crystals to be the 2'-(S)-isomer. The mother liquor was reduced to a volume of about 5 ml, seeded with crystals of the 2'-(R) epioxazoline isomer and refrigerated for 2 days. The crystals (80 mg) were collected by filtration and dried under vacuum at room temperature, n.m.r. analysis showed these crystals to be the 2'-(R) isomer.

Procedure E a. Electrolysis The electrolysis was carried out in essentially the same manner as in Procedure D, except that the cathode potential was −1.55 V.

b. Oxidation NBS (652 mg) was added to the catholyte in the cathode compartment. The catholyte solution was then removed from the cathode compartment, ethyl acetate (60 ml) was added, the layers were separated and the ethyl acetate layer was washed with 1:1 0.3 M (pH 7) phosphate:saturated sodium chloride/1% sodium bisulfite (50 ml, 3X). The ethyl acetate layer was then dried over magnesium sulfate, filtered and the filtrate evaporated to a foam. The foam was dried under vacuum at room temperature to yield 1.3 g of dry foam. The foam was dissolved in acetonitrile/10% water (70 ml), additional NBS (240 mg) was added and the reaction was monitored by HPLC analysis. When the reaction was complete 1:1 0.3 M (pH 7) phosphate:saturated sodium chloride/1% sodium bisulfite (50 ml) was added. Ethyle acetate (80 ml) was added, the layers were separated and the ehtyl acetate layer was washed sequentially with 0.1 N hydrochloric acid saturated with sodium chloride (2X) and 1:1 0.3 M (pH 7) phosphate:saturated sodium chloride/1% sodium bisulfate solution (1X). The ethyl acetate layer was dried over magnesium sulfate, filtered and the filtrate evaporated to yield a foam. The foam was dried under vacuum at room temperature to give 926 mg of a 1:1 mixture of 2'-(R) and 2'-(S) isomers as determined by integration of the respective n.m.r. peaks of the C-5 proton.

Procedure F a. Electrolysis The electrolysis was carried out in the same general manner as in the foregoing procedure except for the following reaction conditions: 1 g of the starting sulfone was dissolved in a methanol solution (37 ml) containing thiophenoxyacetic acid (310 mg, 50 millimoles). The solvent solution was made 0.1 M in sodium perchlorate. The cathode potential was −1.5 V during the electrolysis.

b. Oxidation The catholyte solution was removed from the cathode and extracted twice with ethyl acetate. The ethyl acetate extracts were combined, washed sequentially with 1:1 0.3 M (pH 7) phosphate:saturated sodium chloride solution (50 ml, 3X) and 1:1 5% sodium bicarbonate:saturated sodium chloride solution (100 ml, 1X). The ethyl acetate layer was then dried over magnesium sulfate, filtered and the filtrate evaporated to dryness to yield 630 mg of residue. The residue was dissolved in a 10% water/methanol solution (25 ml). The resultant solution was cooled in an ice-alcohol bath and a methanol solution of NBS (200 mg) was added. After approximately 5 minutes, a 1:1 0.3 M (pH 7) phosphate:saturated sodium chloride/1% sodium bisulfite solution (75 ml) was added. The reaction mixture was then extracted twice with ethyl acetate, the extracts were combined, and washed with 0.1 N hydrochloric acid saturated with sodium chloride (50 ml, 3X). The ethyl acetate solution was then dried over magnesium sulfate, filtered and the filtrate evaporated to dryness to yield 430 mg of a light yellow foam. n.m.r. analysis of this foam showed it to be approximately a 50:50 mixture of 2'-(R) to 2'-(S)-isomers by integration of the n.m.r. at the peaks for the respective C-5 protons.

Procedure G a. Electrolysis Sodium 7-(S)-(p-toluylamido)-3-hydroxymethyl-3-cephem-4-carboxylate (1 g) was added to an aqueous solution (35 ml) of 0.25 M sodium sulfate. This solution was placed in the cathode compartment of an electrolytic cell thermostatted at 0° C. wherein the cell compartments were separated by a cation exchange membrane. The anolyte, a 0.25 M sodium sulfate solution, was then added to the anode compartment. The catholyte was deoxygenated with a stream of argon. The cathode compartment was equipped with a pH stat (obtained from Radiometer A/S, Emdrupve), 72, DK2400, Copenhagen NV, Denmark) set at pH 5 and the pH of the catholyte was maintained between 3.5 and 5.5 using a 0.1 N sulfuric acid titrant. Less than one drop of octanol was added to the cathode compartment to control foaming. The electrolysis was accomplished by applying a −1.85 V to the mercury cathode and maintaining this potential until the current diminshed to approximately zero and HPLC analysis of the catholyte demonstrated that almost all of the starting material was depleted.

b. Oxidation The catholyte solution was removed from the cathode compartment and 1 M phosphate buffer solution (pH 7, 5 ml) and ethyl acetate (50 ml) were added. This solution was chilled in an ice-alcohol bath and the pH was adjusted to 2.5 by the addition of 12 N sulfuric acid. A dimethylformamide solution (2 ml) of N-bromosuccinimide (800 mg) was added dropwise with rapid stirring over a period of approximately five minutes. (The yellow color formed on addition of NBS solution was allowed to dissipate before additional NBS solution was added). Sodium bisulfite (200 mg) was added, the layers were separated and the aqueous layer was extracted with additional ethyl acetate (50 ml). The two ethyl acetate layers were combined and washed with a 1:9 1 N hydrochloric acid:saturated sodium chloride solution (50 ml, 2X). Ice was used liberally throughout the extraction procedure to keep the solution cool. The ethyl acetate layer was dried over magnesium sulfate, filtered and reduced to a volume of approximately 10 ml under high vacuum and low heat and the concentrate was refrigerated overnight. The resultant crystals were filtered under vacuum to yield 406 mg (52% yield) of a 4:1 2'-(S):2'-(R) mixture of the epioxazoline acids. A portion of the crystal mixture (100 mg) was esterified using diphenyldiazomethane. Recrystallization yielded the 1'-esterified-2'-(S)-isomer, as indicated by n.m.r. and f.d.m.s. n.m.r. (2'-(S))-2'-((1R,5S)-3-(p-toluyl)-7-oxo-4-oxa-2,6-diazobicyclo[3.2.0]hept-2-en-6-yl)-4'-hydroxy-3'-exomethylenebutyric acid: n.m.r. (DMSOd$_6$) δ 2.32 (s, 3, p-methyl), 3.92 (s, 2, hydroxymethylene protons), 4.86 (s, 1, C-2' proton), 5.14 (s, 1, C-3' exomethylene proton), 5.34 (s, 1, C-3' exomethylene proton), 5.40 (d, 1, C-1 proton), 6.28 (d, 1, C-5 proton), 7.2 to 7.88 (m, 4, aromatic protons); f.d.m.s. (parent ion) 316 m/e. The benzhedryl ester of this product has an f.d.m.s. of M$^\oplus$ 483.

Procedure H a. Electrolysis The solution of methanol (48 ml) and acetic acid (3.0 ml) was made 0.1 M in sodium acetate. Benzhydryl 7-(S)-(p-toluylamido)-3-hydroxymethyl-3-cephem-4-carboxylate (4.0 g) was added to the solution and the resultant mixture was added to the cathode compartment of an electrolytic cell containing a zinc cathode (24 cm$^2$) thermostatted at 0° C. The electrolysis was conducted at a potential of −1.55 V for a period of about 7500 seconds. At the end of this time, HPLC analysis of the catholyte indicated that the reduction was very near completion and the electrolysis was stopped.

b. NBS Oxidation The catholyte was then transferred to a flask and chilled to 0° C. in an alcohol/ice bath. A methanol solution of N-bromosuccinimide (1.5 equivalents) was added to the chilled catholyte through a dropping funnel. When the HPLC analysis of the resultant reaction mixture indicated that the oxidation of the reaction was complete, a 1:1 0.3 M pH 7 phosphate:saturated sodium chloride solution that was 1% in sodium hydrogen sulfite was added to the reaction mixture, and the resultant solution was extracted twice with ethyl acetate. The ethyl acetate layers were combined, washed three times with 1:1 0.3 M pH 7 phosphate:sodium saturated chloride solution, dried over magnesium sulfate, filtered and evaporated to dryness in vacuo, to yield 3.00 g of white foam. The foam was crystallized from 25% hexane/toluene to yield 2.1 g of crystals of a mixture of 2'-(S) and 2'-(R)-isomers of the title product. m.m.r. (major identifying peaks only) (DMSOd$_6$, reference was TMS): δ 6.18 (d, 1, C-5 proton of 2'-(R)-isomer), 6.38 (d, 1, C-5 proton of 2'-(S)-isomer).

Procedure I a. Electrolysis A solution of methanol (48 ml) and acetic acid (3.0 ml) was made 0.5 M in sodium perchlorate. Benzhydryl 7-(S)-(p-toluylamido)-3-hydroxymethyl-3-cephem-4-carboxylate (4.0 g) was added to this solution and the resultant mixture was added to the cathode compartment of an electrolytic cell containing a zinc cathode (24 cm$^2$) and thermostatted at 0° C. The electrolysis was conducted at −1.40V for about 10,000 seconds.

b. NBS Oxidation When the above electrolysis was completed, the catholyte was transferred to a flask and chilled to 0° C. in an alcohol/ice bath. A methanol solution (approximately 50 ml) of N-bromosuccinimide (1.5 equivalents) was added to the chilled catholyte slowly through a dropping funnel. When the HPLC analysis showed that the oxidation reaction was substantially complete, a 1:1 0.3 M pH 7 phosphate:saturated sodium chloride solution that was 1% in sodium hydrogen sulfite was added to the reaction mixture, and the resultant solution was extracted twice with ethyl acetate. The ethyl acetate layers were combined, washed (3X) with a 1:1 0.3 M pH 7 phosphate:saturated sodium chloride solution, dried over magnesium sulfate, filtered, concentrated and placed in a refrigerator. The chilled concentrate was filtered to yield 1.954 g of about a 1:1 mixture of 2'-(S):2'-(R) isomeric mixture of the title product. n.m.r. (major identifying peaks only) (DMSOd$_6$, reference was TMS): δ 6.18 (d, 1, C-5 proton of the 2'-(R)-isomer), 6.38 (d, 1, C-5 proton of the 2'-(S)-isomer).

EXAMPLE 13

Benzhydryl (2'-(R,S))-2'-[(1R,5S)-3-[D-(4-(2,4-dichlorobenzyloxycarbonylamino)-4-(benzhydryl carboxylate)but-1-yl]-7-oxo-4-oxa-2,6-diazabicyclo-[3.2.0]-hept-2-en-6-yl]-4'-hydroxy-3'-exomethylene butyrate.

a. Electrolysis A solution of 25% water in acetonitrile (34 ml) and acetic acid (2 ml) was made 0.1 M in tetraethylammonium perchlorate. Benzhydryl 7-(S)-[D-(5-(2,4-dichlorobenzoylamino))-5-(benzhydryl carboxylate)valeramido]-3-hydroxymethyl-3-cephem-4-carboxylate sulfone (1 g) was added to this solution. In turn, this solution was added to the cathode compartment of an electrolytic cell thermostatted at 0° C. The electrolysis was carried out by applying a potential of −1.45V to the cathode (vs. a saturated calomel electrode) and maintaining this potential until HPLC analysis of the catholyte solution demonstrated that substantially all of the starting material has been consumed.

b. Lead tetraacetate oxidation The catholyte solution was removed from the cathode compartment and ethyl acetate (90 ml) was added. The layers were separated and the ethyl acetate layer was washed with a 1:1 0.3 M phosphate buffer solution (pH 7):saturated sodium chloride solution (75 ml, 3X). The ethyl acetate layer was dried over sodium sulfate, filtered and the filtrate's volume was reduced to approximately 25 ml. Lead tetraacetate (531 mg) was added and, after ten minutes, the white precipitate which formed was removed by filtration. The ethyl acetate filtrate was washed with a 1:1 phosphate buffer solution (pH 7):saturated sodium chloride solution (4X). The ethyl acetate layer was then dried over sodium sulfate and filtered. The volume of the filtrate was reduced under vacuum to give 4 ml solution containing benzhydryl (2'-(R,S))-2'-[(1R,5S)-3-[D-(4-(2,4-dichlorobenzyloxycarbonylamino)-4-(benzhydryl carboxylate)but-1-yl]-7-oxo-4-oxa-2,6-diazabicyclo[3.2.0]-hept-2-en-6-yl]-4'-hydroxy-3'-exomethylene butyrate.

EXAMPLE 14

N-[Benzhydryl 3'-hydroxymethyl-2'-yl-2'-(R,S)-but-3'-enoate]-2-(R)-(sodium sulfinate)-3-(S)-benzyloxycarbamido)-4-oxo azetidine.

Procedure A

To a solution of dimethylformamide (34 ml) and acetic acid (2 ml) was added sufficient tetraethylammonium perchlorate to give a 0.1 M concentration. Benzhydryl 7-(S)-benzyloxycarbamido-3-hydroxymethyl-3-cephem-4-carboxylate sulfone (1.15 g) was added to the resultant solution. The sulfone-containing solution was added to the cathode compartment of the electrolytic cell. The cell temperature was maintained at 0° C. and the current was maintained at 300 ma throughout the electrolysis. When the electrolysis was completed the cathode solution was removed from the cathode compartment, ethyl acetate (150 ml) was added and this solution was washed with sodium chloride solution made 0.1 N in hydrochloric acid (75 ml, 3X). The ethyl acetate solution was then washed with a 1:1 0.3 M pH 7 phosphate:saturated sodium chloride solution (75 mls, 3X). The ethyl acetate solution was dried over magnesium sulfate, filtered and the solvent removed in vacuo to yield 990 mg of N-[benzhydryl 3'-hydroxymethyl-2'-yl-2'-(R,S)-but-3'-enoate]-2-(R)-(sodium sulfinate)-3-(S)-(benzyloxycarbamido)-4-oxoazetidine.

Procedure B

The electrolysis was conducted on benzhydryl 7-(S)-benzyloxycarbamido-3-hydroxymethyl-4-carboxylate sulfone (562 mg) as in Procedure A, with the following changes: acetonitrile is used as the solvent instead of dimethylformamide, and potential was maintained at −1.450V throughout the electrolysis.

The cathode solution was removed from the cathode compartment, ethyl acetate (100 ml) was added, and the resultant solution was washed with a 1:1 0.3 M pH 7 phosphate:saturated sodium chloride solution (80 ml, 3X). The ethyl acetate solution was dried over magnesium sulfate and filtered to give a solution of the title product.

EXAMPLE 15

Benzhydryl 2'-[(1R,5S)-3-(p-toluyl)-7-oxo-4-oxa-2,6-diazabicyclo[3.2.0]hept-2-en-6-yl]-4'-hydroxy-3'-methylbut-2'-(E,Z)-eneoate.

a. Electrolysis A solution of methanol (36 ml) and acetic acid (0.1 ml) was made 0.1 M in (tri-n-butyl)ammonium para-toluene sulfonate. To this solution was added benzhydryl 7-(S)-toluylamido-3-hydroxymethyl-3-cephem-4carboxylate sulfone (1 g). This solution was added to the cathode compartment of an electrolytic cell. The electrolysis was carried out at a cathode potential of −1.500 V. The electrolysis produced an isomeric mixture of N-(benzhydryl 3'-hydroxymethyl-2'-yl-but-2'-(E,Z)-eneoate)-2-(R)-(sodium sulfinate)-3-(S)-(p-toluylamido)-4-oxo-azetidine.

b. Oxidation The mercury was removed from the cathode compartment and a stoichiometric amount (equal to the equivalents of sulfinic acid produced based on coulometry) of N-bromosuccinimide was added. The reaction was removed from the cathode compartment, and water (twice the volume of the reaction solution) was added. The precipitate was collected by filtration, washed with water and dissolved in ethyl acetate. The ethyl acetate solution was washed with water, dried over magnesium sulfate, filtered and evaporated to dryness in vacuo to give an isomeric mixture of benzhydryl 2'-[(1R,5S)-3-(p-toluyl)-7-oxo-4-oxa-2,6-diazabicyclo[3.2.0]hept-2-en-6-yl]-4'-hydroxy-3'-methylbut-2'-(E,Z)-eneoate.

I claim:

1. A process for preparing a compound of the formula

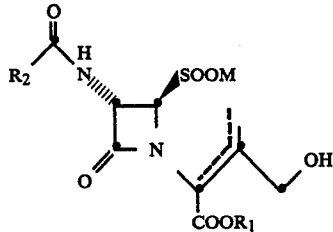

which comprises electrolytically reducing at a potential at or above the reduction potential required for the cleavage of the sulfone to $C_2$ bond of a cephalosporin sulfone compound of the formula

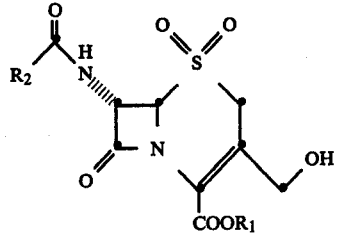

in a solvent chosen from the group consisting of a polar organic solvent, water, and a mixture of the two, all of which are stable under the conditions of the electrolysis, and (a) when the solvent used is a polar organic solvent or a mixture of water and a polar organic solvent, in the presence of a proton source comprised of a carboxylic acid having a pKa between about zero to about five in an amount equal to at least one molar equivalent per molar equivalent of cephalosporin sulfone; or (b) when the solvent used is water, maintaining the pH of the aqueous solution between about three to about nine;

at a temperature above about the freezing point of the solvent to about 40° C.; wherein the electrolytic reduction is carried out in the presence of a catholyte selected from the group consisting of an alkali metal salt, ammonium and substituted ammonium salts.

2. A process of claim 1, wherein the potential is at or below the discharge potential of the solvent.

3. A process of claim 2, wherein the potential is between about −1.0 V to about −1.9 V, compared to a saturated calomel reference electrode.

4. A process of claim 1, wherein a constant current is maintained.

5. A process of claim 4, wherein a constant current density of between about 2 to about 200 ma/cm$^2$ is maintained.

6. A process of claim 1, wherein the cathode is comprised substantially of mercury, lead, zinc, copper, graphite, or cadmium.

7. A process of claim 6, wherein the cathode is comprised substantially of mercury, zinc, or lead.

8. A process of claim 1, wherein the electrolyte is tetraethylammonium perchlorate, sodium perchlorate, lithium chloride, sodium sulfate, sodium acetate, sodium chloride, or tri-n-butylammonium paratoluenesulfonate.

9. A process of claim 1, wherein a compound of the formula

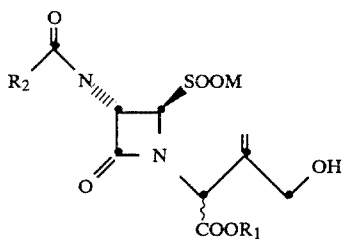

is prepared.

10. A process of claim 9, wherein R$_2$ is a heteroarylmethyl group of the formula

R'''—CH$_2$—.

11. A process of claim 10, wherein R''' is thien-2-yl.

12. A process of claim 11, wherein N-(benzhydryl-3'-hydroxymethyl-2'-yl-2'-(R,S)-but-3'-enoate)-2-(R)-(sodium sulfinate)-3-(S)-[2-(thien-2-yl)-acetamido]-4-oxo-azetidine is prepared by the electrolysis of benzhydryl 7-(S)-[2-(thien-2-yl)acetamido]-3-hydroxymethyl-3-cephem-4-carboxylate sulfone wherein the solvent and electrolyte is methanol and sodium chloride, respectively; or a mixture of dimethylformamide and water and tetraethylammonium perchlorate, respectively.

13. A process of claim 9, wherein R$_2$ is C$_1$–C$_7$ alkyl, C$_3$–C$_7$ alkenyl, chloromethyl, dichloromethyl, 4-carboxybutyl, 4-formylbutyl, 4-protected carboxybutyl, 4-amino-4-carboxybutyl, or 4-protected amino-4-protected carboxybutyl.

14. A process of claim 13, wherein R$_2$ is C$_1$–C$_7$ alkyl, C$_3$–C$_7$ alkenyl, or 4protected amino-4-protected carboxybutyl.

15. A process of claim 14, wherein N-(benzhydryl-3'-hydroxymethyl-2'-yl-2'-(R,S)-but-3'-enoate)-2-(R)-(sodium sulfinate)-3-(S)-[D-(5-(2,4-dichlorobenzoxycarbonylamino))-5-(benzhydryl carboxylate)valeramido]-4-oxo-azetidine is prepared by the electrolysis of benzhydryl 7-(S)-[D-(5-(2,4-dichlorobenzoxycarbonylamino))-5-(benzhydryl carboxylate)valeramido]-3-hydroxymethyl-3-cephem-4-carboxylate sulfone wherein the solvent is a polar organic solvent or a mixture of a polar organic solvent and water and the proton source is acetic acid.

16. A process of claim 15, wherein the solvent is methanol and the electrolyte is sodium perchlorate.

17. A process of claim 15, wherein the solvent is a mixture of acetonitrile and water and the electrolyte is tetraethylammonium perchlorate.

18. A process of claim 15, wherein the solvent is methanol and the electrolyte is sodium acetate.

19. A process of claim 8, wherein R$_2$ is 1,4-cyclohexadienyl, phenyl, or substituted phenyl.

20. A process of claim 19, wherein R$_2$ is phenyl or substituted phenyl, wherein the substituents are one or two substituents chosen from the group consisting of C$_1$–C$_4$ alkyl, alkoxy, and hydroxy.

21. A process of claim 20, wherein N-(benzhydryl-3'-hydroxymethyl-2'-yl-2'-(R,S)-but-3'-enoate)-2-(R)-(sodium sulfinate)-3-(S)-(p-toluylamido)-4-oxoazetidine is prepared by the electrolysis of benzhydryl 7-(S)-(p-toluylamido)-3-hydroxymethyl-3-cephem-4-carboxylate sulfone wherein the solvent is methanol, a mixture of methanol and water, or a mixture of acetonitrile and water, the proton source is acetic acid, benzoic acid, or 2-(thiophenoxy)acetic acid, the temperature is between about −10° C. to about 10° C., and the electrolyte is lithium chloride, sodium perchlorate or sodium acetate.

22. A process of claim 20, wherein N-(3'-hydroxymethyl-2'-yl-2'-(R,S)-but-3'-enoic acid)-2-(R)-(sulfinic acid)-3-(S)-(p-toluylamido)-4-oxoazetidine is prepared by the electrolysis of sodium 7-(S)-(p-toluylamido)-3-hydroxymethyl-3-cephem-4-carboxylate sulfone wherein water is the solvent, sodium sulfate is the electrolyte, sulfuric acid is the proton source, and the temperature is between about 5° C. to about 20° C., or wherein the solvent is water, the electrolyte is sodium chloride, the proton source is hydrochloric acid, and the temperature is between about 5° C. to about 20° C.

23. A process of claim 9, wherein R$_2$ is C$_1$–C$_6$ alkoxy, C$_3$–C$_6$ cycloalkyloxy, benzyloxy, or substituted benzyloxy, wherein the substituents are one to three groups chosen from the group consisting of C$_1$–C$_4$ alkyl, C$_1$–C$_4$ alkoxy, or chloro.

24. A process of claim 23, wherein N-(benzhydryl-3'-hydroxymethyl-2'-yl-2'-(R,S)-but-3'-enoate)-2-(S)-(sodium sulfinate)-3-(S)-(benzyloxycarbamido)-4-azetidine is prepared by the electrolysis of benzhydryl 7-(S)-benzyloxycarbamido-3-hydroxymethyl-3-cephem-4-carboxylate sulfone, wherein the solvent is a polar organic solvent or a mixture of a polar organic solvent and water and the temperature between about −10° C. to about 10° C.

25. A process of claim 24, wherein the electrolyte is tetraethylammmonium perchlorate, and the solvent is acetonitrile or dimethylformamide.

26. A process of claim 9, wherein R$_2$ is an arylalkyl group of the formula

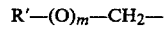

R'—(O)$_m$—CH$_2$— wherein R' is phenyl or substituted phenyl wherein the substituents are one or two substituents chosen from the group consisting of chlorine, bromine, hydroxy, trifluoromethyl, C$_1$–C$_4$ alkyl, C$_1$–C$_4$ alkoxy, carboxy, carboxymethyl, hydroxymethyl, aminomethyl, and protected aminomethyl, and m is 0 or 1.

27. A process of claim 26, wherein m is 1 and the temperature is between about −10° C. to about 20° C.

28. A process of claim 27, wherein N-(benzhydryl 3'-hydroxymethyl-2'-yl-2'-(R,S)-but-3'-enoate)-2-(R)-(sodium sulfinate)-3-(S)-(2-phenoxyacetamido)-4-oxoazetidine is prepared by the electrolysis of benzhydryl 7-(S)-(2-phenoxyacetamido)-3-hydroxymethyl-3-cephem-4-carboxylate sulfone wherein the solvent is methanol, the proton source is acetic acid, and the electrolyte is tetraethylammonium perchlorate.

29. A process of claim 27, wherein N-(sodium 3'-hydroxymethyl-2'-yl-2'-(R,S)-but-3'-enoate)-2-(R)-(sodium sulfinate)-3-(S)-(2-phenoxyacetamido)-4oxo-azetidine is prepared by the electrolysis of sodium 7-(S)-(2-phenoxyacetamido)-3-hydroxymethyl-3-cephem-4-carboxylate sulfone and wherein the solvent is water, the temperature is between about 5° C. to about 20° C., the proton source is sulfuric acid, and the electrolyte is sodium sulfate.

30. A process of claim 26, wherein m is 0, the temperature is between about −10° C. to about 10° C. and the solvent is a polar organic solvent or a mixture of a polar organic solvent and water.

31. A process of claim 30, wherein N-(benzhydryl 3'-hydroxymethyl-2'-yl-2'-(R,S)-but-3'-enoate)-2-(R)-(sodium sulfinate)-3-(S)-(2-phenylacetamido)-4-oxo-azetidine is prepared by the electrolysis of benzhydryl 7-(S)-(2-phenylacetamido)-3-hydroxymethyl-3-cephem-4-carboxylate sulfone and wherein the solvent is methanol, the proton source is acetic acid, and the electrolyte is sodium perchlorate.

* * * * *

UNITED STATES PATENT AND TRADEMARK OFFICE
CERTIFICATE OF CORRECTION

PATENT NO. : 4,436,596　　　　　　　　　　Page 1 of 3
DATED : March 13, 1984
INVENTOR(S) : David A. Hall It is certified that error appears in the above—identified patent and that said Letters Patent is hereby corrected as shown below:

In the claims, after the formula at column 46, lines 19 through 29, insert

-- wherein,

M is hydrogen or is a lithium, potassium, sodium, ammonium or a substituted ammonium cation;

$R_1$ is hydrogen, a carboxylic acid protecting group, lithium, potassium, sodium, ammonium or substituted ammonium cation;

$R_2$ is
- a. $C_1$ to $C_7$ alkyl, $C_3$ to $C_7$ alkenyl, chloromethyl, dichloromethyl, 4-carboxybutyl, 4-formylbutyl, 4-amino-4-carboxybutyl, or 4-protected carboxybutyl, 4-protected amino-4-protected carboxybutyl; or
- b. $C_1$ to $C_6$ alkoxy, $C_3$ to $C_6$ cycloalkyloxy, benzyloxy or substituted benzyloxy, wherein the substituents are one to three groups chosen from the group consisting of $C_1$ to $C_4$ alkyl, $C_1$ to $C_4$ alkoxy or chloro; or

UNITED STATES PATENT AND TRADEMARK OFFICE
CERTIFICATE OF CORRECTION

PATENT NO. : 4,436,596

DATED : March 13, 1984

INVENTOR(S) : David A. Hall

It is certified that error appears in the above—identified patent and that said Letters Patent is hereby corrected as shown below:

c. 1,4-cyclohexadienyl, phenyl or substituted phenyl, wherein the substituents are one or two groups chosen from the group consisting of chlorine, bromine, hydroxy, trifluoromethyl, $C_1$ to $C_4$ alkyl, $C_1$ to $C_4$ alkoxy, carboxy, carboxymethyl, hydroxymethyl, aminomethyl and protected aminomethyl; or d. an arylalkyl group of the formula $$R'-(O)_m-CH_2-$$

wherein R' is 1,4-cyclohexadienyl, phenyl or substituted phenyl as defined above, and m is 0 or 1; or e. a substituted arylalkyl group of the formula $$R''-\underset{W}{\overset{H}{\underset{|}{\overset{|}{C}}}}-$$

wherein R'' is R' as defined above, 2-thienyl, or 3-thienyl; W is hydroxy, carboxy, protected carboxy, amino or protected amino; or f. a heteroarylmethyl group of the formula $$R'''-CH_2$$

wherein R''' is 2-thienyl, 3-thienyl, 2-furyl, 3-furyl, 2-thiazolyl, 5-tetrazolyl or 1-tetrazolyl;

with the limitation that when the compound is of the formula

UNITED STATES PATENT AND TRADEMARK OFFICE
CERTIFICATE OF CORRECTION

PATENT NO.   :   4,436,596              Page 3 of 3
DATED        :   March 13, 1984
INVENTOR(S)  :   David A. Hall It is certified that error appears in the above-identified patent and that said Letters Patent is hereby corrected as shown below:

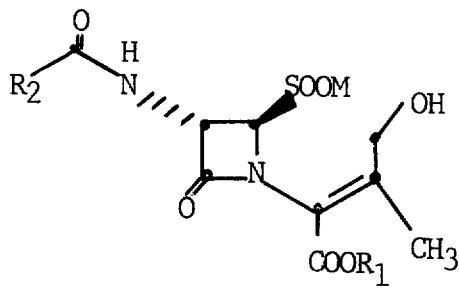

$R_2$ is 1,4-cyclohexadienyl, phenyl or substituted phenyl, wherein the substituents are one or two groups chosen from the group consisting of chlorine, bromine, hydroxy, trifluoromethyl, $C_1$ to $C_4$ alkyl, $C_1$ to $C_4$ alkoxy, carboxy, carboxymethyl, hydroxymethyl, aminomethyl and protected aminomethyl. --

Signed and Sealed this

Eighth Day of January 1985

[SEAL]

Attest:

GERALD J. MOSSINGHOFF

Attesting Officer

Commissioner of Patents and Trademarks